United States Patent
Kosuge et al.

(10) Patent No.: US 8,129,899 B1
(45) Date of Patent: Mar. 6, 2012

(54) AZAFLUORENE DERIVATIVE AND ORGANIC LIGHT-EMITTING DEVICE USING THE DERIVATIVE

(75) Inventors: Tetsuya Kosuge, Kawasaki (JP); Akihiro Senoo, Kawasaki (JP); Hiroki Ohrui, Kawasaki (JP); Masanori Muratsubaki, Hachioji (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/289,345

(22) Filed: Nov. 4, 2011

Related U.S. Application Data

(62) Division of application No. 11/961,801, filed on Dec. 20, 2007.

(30) Foreign Application Priority Data

Dec. 26, 2006 (JP) .................. 2006-349580

(51) Int. Cl.
*H01J 1/62* (2006.01)
(52) U.S. Cl. ...................................... 313/504
(58) Field of Classification Search ................ 313/504
See application file for complete search history.

(56) References Cited

U.S. PATENT DOCUMENTS

| 6,620,821 | B2 | 9/2003 | Robl |
| 2006/0166034 | A1 | 7/2006 | Saitoh et al. |
| 2007/0228941 | A1 | 10/2007 | Abe et al. |

FOREIGN PATENT DOCUMENTS

| JP | 2005-314613 | 11/2005 |
| WO | 93/14080 | 7/1993 |
| WO | 2006/081973 | 8/2006 |

OTHER PUBLICATIONS

Wong et al., "Modulation of Physical Properties of Ter(9,9-ditolylfluorene) by Backbone-Embedded Heteroarenes" Org. Lett., vol. 8, No. 7, pp. 1415-1418 (2006).
Goerlitzer et al., Phamazie 1998, 53, 303-307.
Prostakov et al., Chemistry of Heterocyclic Compounds 2004, 19, 519-521 as translated from Khimiya Geterotsiklicheskikh Soedinenii 1984, 5, 648-650.
Solov'yanov, et al., Zhurnal Organicheskoi Khimii 1983, 19, 1822-1835—English Translation.

*Primary Examiner* — Janet Andres
*Assistant Examiner* — John Mabry
(74) *Attorney, Agent, or Firm* — Fitzpatrick, Cella, Harper & Scinto

(57) ABSTRACT

A novel azafluorene derivative and an organic light-emitting device having the derivative are provided. The organic light-emitting device includes a pair of electrodes composed of an anode and a cathode one of which is a transparent or semi-transparent electrode, and an organic compound layer interposed between the pair of electrodes. The organic compound layer contains the azafluorene derivative represented by the following general formula (I):

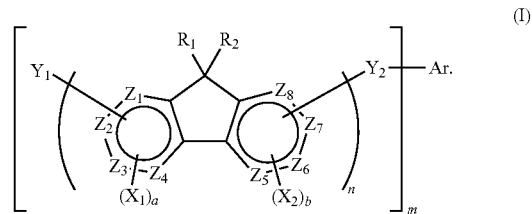

6 Claims, 2 Drawing Sheets

AZAFLUORENE DERIVATIVE AND ORGANIC LIGHT-EMITTING DEVICE USING THE DERIVATIVE

The present application is a divisional of U.S. patent application Ser. No. 11/961,801 filed Dec. 20, 2007, the entire disclosure of which is incorporated by reference herein.

BACKGROUND OF THE INVENTION

1. Field of the Invention

The present invention relates to a novel azafluorene derivative and an organic light-emitting device using the derivative.

2. Description of the Related Art

An organic light-emitting device is a device having a thin film which contains a fluorescent or phosphorescent organic compound and is interposed between electrodes. Electrons and holes are injected from the respective electrodes, whereby excitons of the fluorescent or phosphorescent compound are produced. The excitons emit light when they return to their ground states.

The development of an organic light-emitting device is remarkable, and the characteristics of the device are such that luminance is high at low applied voltage, lights with various wavelengths can be emitted, the speed of response is high, its thickness is thin and its weight is light. Accordingly, the device has potential for a variety of applications.

However, the present situation calls for optical output with higher luminance or higher conversion efficiency. In addition, many problems still remain unsolved regarding durability against changes over time due to long-term use, and deterioration caused by atmospheric gas containing oxygen or moisture. Further, when considering application to a full color display, the present art is still insufficient to address problems concerning need for light emission of blue, green, and red with high color purity.

In the organic light-emitting device, an electron transport layer in contact with a light-emitting layer on the cathode side, an electron injection layer and a hole-blocking layer are not directly involved in the light emission of the device. However, each of the layers largely affects the light-emitting characteristic and durability of the device from the viewpoint of, for example, a carrier balance in the light-emitting layer. In general, heterocyclic derivatives are often used in the electron transport layer.

Azafluorene derivatives are included in the heterocyclic derivatives, and the case where an azafluorene derivative is used in an organic light-emitting device is described in, for example, each of Japanese Patent Application Laid-Open No. 2005-314663, WO 2006/081973, and Org. Lett., 8, 1415 (2006). In each of Japanese Patent Application Laid-Open No. 2005-314663 and WO 2006/081973, an azafluorene derivative is used as a ligand of a metal complex in an organic light-emitting device. Org. Lett., 8, 1415 (2006) proposes that an azafluorene derivative whose azafluorene ring is substituted by an aryl group at the 9-position is used in an organic light-emitting device. However, there is no report on an example in which an azafluorene derivative obtained by substituting 9-position of an azafluorene ring by an alkyl group is used by itself and not as a ligand of a metal complex in an organic light-emitting device, in particular, in an electron transport layer.

SUMMARY OF THE INVENTION

An object of the present invention is to provide a novel azafluorene derivative. The compound can be used as, for example, a material for an organic light-emitting device. In addition, another object of the present invention is to provide an organic light-emitting device which uses the material for an organic light-emitting device and has good emission efficiency and high durability. Further, still another object of the present invention is to provide an organic light-emitting device that can be easily produced at a relatively low cost.

The inventors of the present invention have made extensive studies with the view to solving the above-mentioned problems.

As a result, the inventors have completed the present invention.

The present invention provides an azafluorene derivative represented by the following general formula (I):

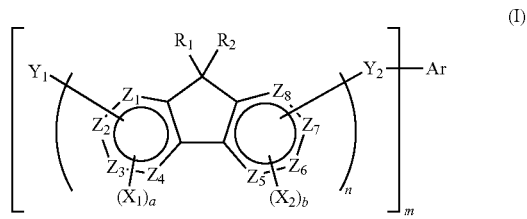

where: n and m each independently represent an integer of 1 to 4, a represents an integer of 0 to 4, and b represents an integer of 0 to 3; one of $Z_1$ to $Z_8$ represents a nitrogen atom, and the other seven each represent a carbon atom; $Y_1$ represents a substituent selected from the group consisting of a hydrogen atom, a substituted or unsubstituted aromatic hydrocarbon group, and a substituted or unsubstituted heterocyclic group; $Y_2$ represents a single bond, a divalent aromatic hydrocarbon group which may be substituted, or a divalent heterocyclic group which may be substituted; $X_1$ and $X_2$ each independently represent a substituent selected from the group consisting of a substituted or unsubstituted alkyl group, a substituted or unsubstituted alkoxy group, a substituted or unsubstituted aromatic hydrocarbon group, a substituted or unsubstituted heterocyclic group, and a substituted amino group; Ar represents an m-valent aromatic hydrocarbon group which may be substituted or an co-valent heterocyclic group which may be substituted, provided that Ar may represent a hydrogen atom when m represents 1; $R_1$ and $R_2$ each independently represent an alkyl group which is unsubstituted or may be substituted by a fluorine atom; when a represents 2 or more, $X_1$'s may be identical to or different from each other; when b represents 2 or more, $X_2$'s may be identical to or different from each other; when n represents 2 or more, the types of coupled azafluorene units may be identical to or different from each other; and when m represents 2 or more, $Y_1$'s or $Y_2$'s may be identical to or different from each other, and the number and types of azafluorene units coupled with Ar through $Y_2$ may be identical to or different from each other.

The novel azafluorene derivative of the present invention has high chemical stability, and is excellent in electron transport performance. Accordingly, the derivative can be used as a material for an organic light-emitting device. In particular, an organic light-emitting device using the novel azafluorene derivative in its electron transport layer can be driven at low voltage, has good emission efficiency, and has high durability in long-term driving. In addition, an organic light-emitting device of the present invention can be produced by employing, for example, a vacuum deposition method or a casting method, and a large-area device can be easily produced at a relatively low cost.

Further features of the present invention will become apparent from the following description of exemplary embodiments with reference to the attached drawings.

DESCRIPTION OF THE EMBODIMENTS

Figure 1:
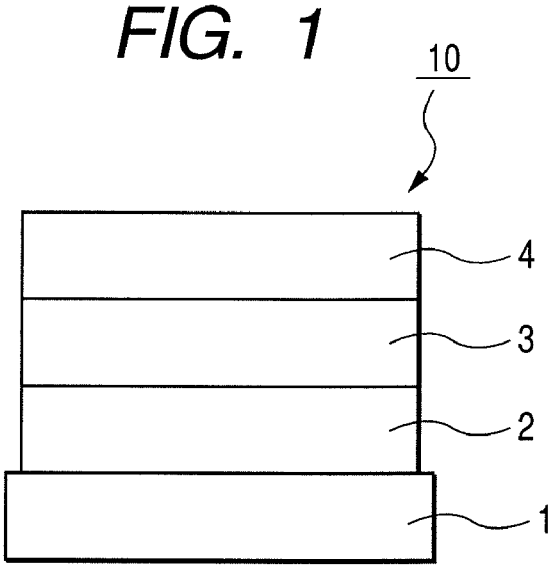
FIG. 1 is a sectional view showing the first embodiment of the organic light-emitting device of the present invention.

Hereinafter, the present invention will be described in detail.

First, an azafluorene derivative of the present invention will be described. The azafluorene derivative of the present invention as a material for an organic light-emitting device will be described.

The material for an organic light-emitting device of the present invention is an azafluorene derivative represented by the following general formula (I).

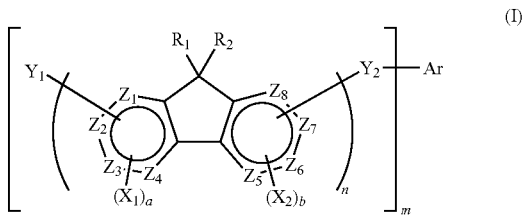

In the formula (I), one of $Z_1$ to $Z_8$ represents a nitrogen atom, and the other seven each represent a carbon atom.

In the formula (I), $Y_1$ represents a substituent selected from the group consisting of a hydrogen atom, a substituted or unsubstituted aromatic hydrocarbon group, and a substituted or unsubstituted heterocyclic group.

Examples of the aromatic hydrocarbon group represented by $Y_1$ include, but are not limited to, a phenyl group, a naphthyl group, an azulenyl group, an indenyl group, an anthracenyl group, a phenanthryl group, a pyrenyl group, a chrysenyl group, a dibenzochrysenyl group, a benzoanthracenyl group, dibenzoanthracenyl group, a naphtacenyl group, a picenyl group, a pentacenyl group, a fluorenyl group, a biphenylenyl group, a triphenylenyl group, a fluoranthenyl group, a benzofluoranthenyl group, and a perylenyl group.

Examples of the heterocyclic group represented by $Y_1$ include, but are not limited to, a pyridyl group, a pyridazyl group, a pyrimidinyl group, a pyrazinyl group, a triazinyl group, a quinolyl group, an isoquinolyl group, a phthalazinyl group, a quinazolinyl group, a quinoxalinyl group, a naphthylidinyl group, an acridinyl group, a phenanthrolyl group, a diazafluorenyl group, phenadinyl group, a pyrrolyl group, a pyrazolyl group, an imidazolyl group, a triazolyl group, an indolyl group, an indolizinyl group, a benzoimidazolyl group, a carbazolyl group, a benzocarbazolyl group, a thienyl group, a benzothienyl group, a dibenzothienyl group, a furyl group, a benzofuryl group, an isobenzofuryl group, a dibenzofuryl group, an oxazolyl group, an isoxazolyl group, a benzoxazolyl group, an oxadiazolyl group, a thiazolyl group, an isothiazolyl group, a benzothiazolyl group, and a thiadiazolyl group.

Examples of substituents with which the aromatic hydrocarbon group and the heterocyclic group may be substituted include, but are not limited to, alkyl groups such as a methyl group, an ethyl group, and a tert-butyl group; aromatic hydrocarbon groups such as a phenyl group, a naphthyl group, a fluorenyl group, and a phenanthryl group; heterocyclic groups such as a thienyl group, a pyrrolyl group, a pyridyl group, and a quinolyl group; substituted amino groups such as a dimethylamino group, a diethylamino group, a dibenzylamino group, and a diphenylamino group; alkoxy groups such as a methoxy group and an ethoxy group; halogen atoms such as fluorine, chlorine, bromine, and iodine; hydroxyl groups; cyano groups; and nitro groups.

In the formula (I), $Y_2$ represents a single bond, a divalent aromatic hydrocarbon group which may be substituted, or a divalent heterocyclic group which may be substituted.

Examples of the aromatic hydrocarbon group represented by $Y_2$ include, but are not limited to, a benzene-1,2-diyl group, a benzene-1,3-diyl group, a benzene-1,4-diyl group, a napthalene-1,4-diyl group, a naphthalene-2,7-diyl group, a phenanthrene-2,7-diyl group, a fluorene-2,7-diyl group, a fluorene-3,6-diyl group, an anthracene-2,6-diyl group, an anthracene-9,10-diyl group, and a pyrene-1,3-diyl group.

Examples of the heterocyclic group represented by $Y_2$ include, but are not limited to a pyridine-2,4-diyl group, a pyridine-2,6-diyl group, a quinoline-2,4-diyl group, a [1,8]naphthylidine-2,7-diyl group, a [1,8]naphthylidine-3,6-diyl group, a [4,5]diazafluorene-2,7-diyl group, a [1,10]phenanthroline-2,9-diyl group, and a 1,3,4-oxadiazole-2,5-diyl group.

Examples of substituents with which the divalent aromatic hydrocarbon group and the divalent heterocyclic group may be substituted include, but are not limited to, alkyl groups such as a methyl group, an ethyl group, and a tert-butyl group; aromatic hydrocarbon groups such as a phenyl group, a naphthyl group, a fluorenyl group, and a phenanthryl group; heterocyclic groups such as a thienyl group, a pyrrolyl group, a pyridyl group, and a quinolyl group; substituted amino groups such as a dimethylamino group, a diethylamino group, a dibenzylamino group, and a diphenylamino group; alkoxy groups such as a methoxy group and an ethoxy group; halogen atoms such as fluorine, chlorine, bromine, and iodine; hydroxyl groups; cyano groups; and nitro groups.

In the formula (I), $X_1$ and $X_2$ each independently represent a substituent selected from the group consisting of a substituted or unsubstituted alkyl group, a substituted or unsubstituted alkoxy group, a substituted or unsubstituted aromatic hydrocarbon group, a substituted or unsubstituted heterocyclic group, and a substituted amino group.

Examples of the alkyl groups represented by $X_1$ and $X_2$ include, but are not limited to, a methyl group, an ethyl group, an n-propyl group, an n-butyl group, an n-pentyl group, an n-hexyl group, an n-heptyl group, an n-octyl group, an n-decyl group, an iso-propyl group, an iso-propyl-d7 group, an iso-butyl group, a sec-butyl group, a tert-butyl group, a tert-butyl-d9 group, an iso-pentyl group, a neopentyl group, a tert-octyl group, a cyclopropyl group, a cyclobutyl group, a cyclopentyl group, a cyclohexyl group, a norbornyl group, and an adamantyl group.

Examples of the alkoxy groups represented by $X_1$ and $X_2$ include, but are not limited to, alkyloxy groups having the above alkyl groups such as a methoxy group, an ethoxy group, a n-propoxy group, an iso-propoxy group, a n-butoxy group, a tert-butoxy group, and a cyclohexyloxy group.

Examples of the aromatic hydrocarbon groups represented by $X_1$ and $X_2$ include, but are not limited to, a phenyl group, a naphthyl group, an azulenyl group, an indenyl group, an anthracenyl group, a phenanthryl group, a pyrenyl group, a chrysenyl group, a dibenzochrysenyl group, a benzoanthracenyl group, a dibenzoanthracenyl group, a naphthacenyl group, a picenyl group, a pentacenyl group, a fluorenyl group, a biphenylenyl group, a triphenylenyl group, a fluoranthenyl group, a benzofluoranthenyl group, and a perylenyl group.

Examples of the heterocyclic groups represented by $X_1$ and $X_2$ include, but are not limited to, a pyridyl group, a pyridazyl group, a pyrimidinyl group, a pyrazinyl group, a triazinyl group, a quinolyl group, an isoquinolyl group, a phthalazinyl group, a quinazolinyl group, a quinoxalinyl group, a naphthylidinyl group, an acridinyl group, a phenanthrolyl group, a diazafluorenyl group, phenadinyl group, a pyrrolyl group, a pyrazolyl group, an imidazolyl group, a triazolyl group, an indolyl group, an indolizinyl group, a benzoimidazolyl group, a carbazolyl group, a benzocarbazolyl group, a thienyl group, a benzothienyl group, a dibenzothienyl group, a furyl group, a benzofuryl group, an isobenzofuryl group, a dibenzofuryl group, an oxazolyl group, an isoxazolyl group, a benzoxazolyl group, an oxadiazolyl group, a thiazolyl group, an isothiazolyl group, a benzothiazolyl group, and a thiadiazolyl group.

Examples of the substituted amino groups represented by $X_1$ and $X_2$ include, but are not limited to, a dimethylamino group, a diethylamino group, a dibenzylamino group, a diphenylamino group, a ditolylamino group, a dianisolylamino group, a fluorenylphenylamino group, a difluorenylamino group, a naphthylphenylamino group, and a dinaphthylamino group.

Examples of substituents with which the alkyl group, the alkoxy group, the aromatic hydrocarbon group and the heterocyclic group may be substituted include, but are not limited to, alkyl groups such as a methyl group, an ethyl group, and a tert-butyl group; aromatic hydrocarbon groups such as a phenyl group, a naphthyl group, a fluorenyl group, and a phenanthryl group; heterocyclic groups such as a thienyl group, a pyrrolyl group, a pyridyl group, and a quinolyl group; amino groups such as a dimethylamino group, a diethylamine group, a dibenzylamino group, and a diphenylamino group; alkoxy groups such as a methoxy group and an ethoxy group; halogen atoms such as fluorine, chlorine, bromine, and iodine; hydroxyl groups; cyano groups; and nitro groups.

In the formula (I), Ar represents an m-valent aromatic hydrocarbon group which may be substituted or an m-valent heterocyclic group which may be substituted.

The m-valent aromatic hydrocarbon group is constituted of an aromatic hydrocarbon ring or an aromatic hydrocarbon ring. Examples of the aromatic hydrocarbon ring or aromatic hydrocarbon ring include, but are not limited to, benzene, naphthalene, azulene, indene, anthracene, phenanthrene, pyrene, chrysene, dibenzochrysene, benzoanthracene, dibenzoanthracene, naphthacene, picene, pentacene, fluorene, biphenylene, triphenylene, fluoranthene, benzofluoranthene, perylene, biphenyl, o-terphenyl, m-terphenyl, p-terphenyl, binaphthyl, phenylnaphthalene, and phenylfluorene.

The m-valent heterocyclic group is constituted of a heterocyclic ring or a heterocyclic ring. Examples of the heterocyclic ring or heterocyclic ring include, but are not limited to, pyridine, pyridazine, pyrimidine, pyradine, triazine, quinoline, isoquinoline, phthalazine, quinazoline, quinoxaline, naphthyridine, acridine, phenanthroline, diazafluorene, phenazine, pyrrole, pyrazole, imidazole, triazole, indole, indolizine, benzoimidazole, carbazole, benzocarbazole, thiophene, benzothiophene, dibenzothiophene, furan, benzofuran, dibenzofuran, oxazole, benzoxazole, oxadiazole, thiazole, benzothiazole, thiadiazole, dihydrophenanthroline, phenanthridine, bipyridine, and dioxazolobenzene.

Ar may represent a hydrogen atom when m represents 1.

In the formula (I), $R_1$ and $R_2$ each independently represent an alkyl group which is unsubstituted or may be substituted by a fluorine atom.

Examples of the alkyl groups represented by $R_1$ and $R_2$ include, but are not limited to, a methyl group, an ethyl group, an n-propyl group, an n-butyl group, an n-pentyl group, an n-hexyl group, an n-heptyl group, an n-octyl group, an n-decyl group, an iso-propyl group, an iso-propyl-d7 group, an iso-butyl group, a sec-butyl group, a tert-butyl group, a tert-butyl-d9 group, an iso-pentyl group, a neopentyl group, a tert-octyl group, a cyclopropyl group, a cyclobutyl group, a cyclopentyl group, a cyclohexyl group, a norbornyl group, and an adamantyl group.

In addition, a hydrogen atom in the azafluorene derivative represented by the formula (I) may be replaced with a deuterium atom.

In the formula (I), n represents an integer of 1 to 4, and represents the number of coupled azafluorene units.

In the formula (I), m represents an integer of 1 to 4, and represents the number of azafluorene units or the groups of the units bonded to Ar through $Y_2$.

In the formula (I), a represents an integer of 0 to 4.

In the formula (I), b represents an integer of 0 to 3.

When a represents 2 or more, $X_1$'s may be identical to or different from each other. In addition, when b represents 2 or more, $X_2$'s may be identical to or different from each other. When n represents 2 or more, coupled azafluorene units may be identical to or different from each other. When m represents 2 or more, $Y_1$'s or $Y_2$'s may be identical to or different from each other, and the numbers or types of azafluorene units coupled with Ar through $Y_2$ may be identical to or different from each other.

The azafluorene derivative represented by the formula (I) is preferably a compound represented by the following general formula (II).

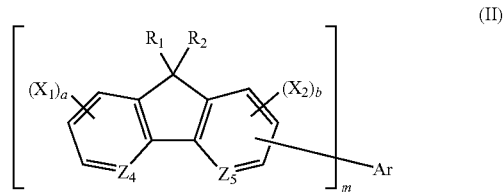

In the formula (II), one of $Z_4$ and $Z_5$ represents a nitrogen atom, and the other represents a carbon atom.

In the formula (II), m, a, b, $X_1$, $X_2$, Ar, $R_1$, and $R_2$ each have the same meaning as defined in the general formula (I).

The azafluorene derivative represented by the formula (I) is more preferably a compound represented by the following general formula (III).

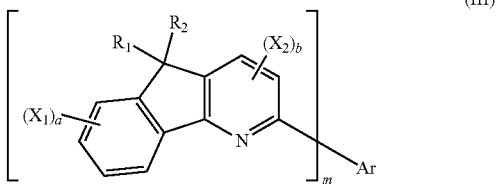

(III)

In the formula (III), m, a, b, $X_1$, $X_2$, Ar, $R_1$, and $R_2$ each have the same meaning as defined in the general formula (I).

The azafluorene derivative represented by the formula (I) is more preferably a compound represented by the following general formula (IV).

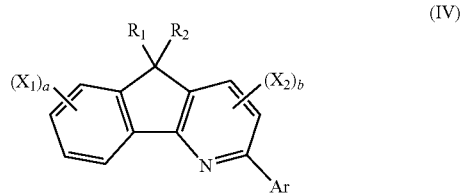

(IV)

In the formula (IV), a, b, $X_1$, $X_2$, Ar, $R_1$, and $R_2$ each have the same meaning as defined in the general formula (I).

A suitable example of the azafluorene derivative represented by the formula (I) is a compound represented by the following general formula (V).

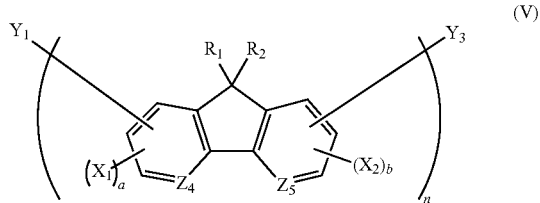

(V)

In the formula (V), one of $Z_4$ and represents a nitrogen atom, and the other represents a carbon atom.

In the formula (V), $Y_3$ represents a group selected from the group consisting of a hydrogen atom, a substituted or unsubstituted aromatic hydrocarbon group, and a substituted or unsubstituted heterocyclic group.

Examples of the aromatic hydrocarbon group represented by $Y_3$ include the same substituents as those represented by $Y_1$ of the general formula (I).

Examples of the heterocyclic group represented by $Y_3$ include the same substituents as those represented by $Y_1$ of the general formula (I).

Examples of the substituents with which the above aromatic hydrocarbon group and the above heterocyclic group may be substituted include the same substituents as those with which $Y_1$ of the general formula (I) may be substituted.

In the formula (V), n, a, b, $Y_1$, $X_1$, $X_2$, Ar, $R_1$, and $R_2$ each have the same meaning as defined in the general formula (I).

The material for the organic light-emitting device of the present invention can be preferably used as an electron transport material. When using the material for the organic light-emitting device of the present invention as an electron transport material, the light-emitting characteristic of the organic light-emitting device can be improved.

With regard to an improvement in light-emitting characteristics of an organic light-emitting device, when using as an electron transport material in an electron transport layer a material which is excellent in electron transport property and facilitates injection of electrons into a light-emitting layer, it is expected that a voltage at which the device is driven is reduced, the emission efficiency of the device increases, and the lifetime of the device is elongated. In such a case, electrons can be efficiently injected into the light-emitting layer at a low driving voltage, and an environment in which material degradation such as carrier accumulation may be promoted can be eliminated.

In order to enhance electron transport performance, it is considered that it is useful to introduce a heteroaromatic ring which has a wide n-conjugated system and is capable of enlarging the extent to which its n-conjugated plane overlaps with that of an adjacent molecule. In the present invention, a compound having an azafluorene ring is introduced as an electron transport material. The azafluorene ring has not only a large n-conjugated system but also a planar structure not present in phenylpyridine that has been conventionally used. Accordingly, the molecular orbital of the azafluorene derivative overlaps with that of an adjacent molecule to a large extent, and the derivative is expected to have excellent electron transport performance. Further, the azafluorene ring has a band gap larger than a phenanthroline ring or a quinoline ring by virtue of distortion caused by its central five-membered ring. Therefore, the HOMO level of the azafluorene derivative is lower than that of a phenanthroline derivative or a quinoline derivative as long as the LUMO level of the azafluorene derivative is maintained at the same level as that of the phenanthroline derivative or the quinoline derivative. Since a material having a low HOMO level exhibits high hole-blocking properties, when using the azafluorene derivative in the electron transport layer, carriers can be inhibited from leaking out of the light-emitting layer, and light emission with high efficiency can be expected.

However, in an azafluorene compound whose which azafluorene ring is not substituted at the 9-position, a carbon atom having high reaction activity is present at the 9-position, and the carbon atom has active hydrogen. Therefore, when the azafluorene compound whose azafluorene ring is not substituted at the 9-position is used in the electron transport layer, radical anions produced during the course of transporting electrons may be chemically unstable. In addition, the instability may cause material degradation such as heat decomposition at the time of driving the device to remarkably degrade the light-emitting characteristic of the device.

With the aim of solving this problem, a substituent need be introduced to the azafluorene ring at the 9-position. In this case, an aryl group is often introduced at the 9-position because a target compound can be synthesized by a simple method. However, a quaternary carbon atom to which four aryl groups are bonded is present even in a 9,9-diaryl-substituted azafluorene compound having aryl groups introduced at the 9-position, and hence, a tertiary carbon radical is apt to be produced by heat decomposition. Accordingly, the heat stability of the compound itself is reduced. Therefore, even when an azafluorene compound whose azafluorene ring is substituted with an aryl group is used in an electron transport layer, the light-emitting characteristic of an organic light-emitting device may deteriorate as in the case of an azafluorene compound whose azafluorene ring is not substituted at the 9-position.

In view of the foregoing, the azafluorene ring of the azafluorene derivative used as the material for the organic light-emitting device of the present invention is substituted by an alkyl group at the 9-position. Thus, the compound itself has a chemically and thermally stable structure, and can be inhibited from undergoing material degradation due to heat decomposition when being used in an organic light-emitting device.

As described above, the material for the organic light-emitting device of the present invention can exert electron injection/transport properties and hole-blocking properties intrinsic to the above-mentioned azafluorene derivative in an organic light-emitting device and improve the light-emitting characteristic of the organic light-emitting device.

The specific structural formulae of the azafluorene derivative as the material for the organic light-emitting device of the present invention are shown below. However, the azafluorene derivative of the present invention is by no means limited to the following structural formulae.

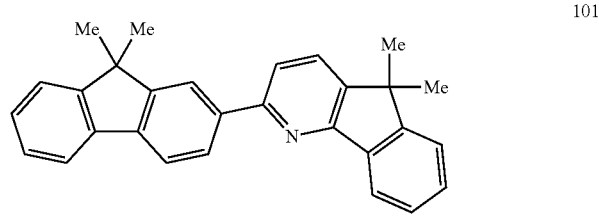

101

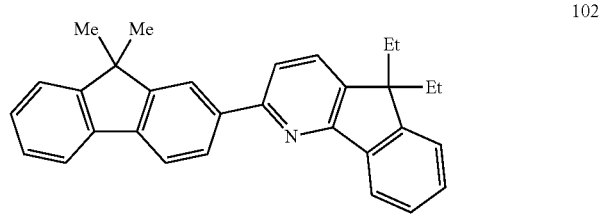

102

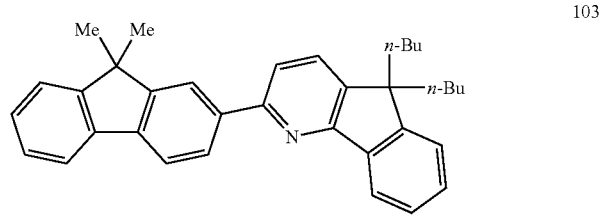

103

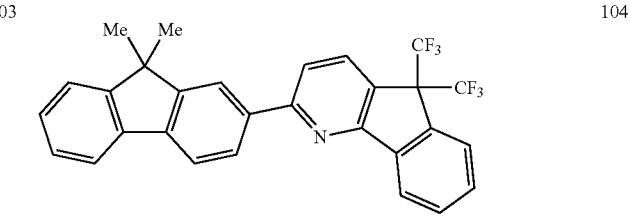

104

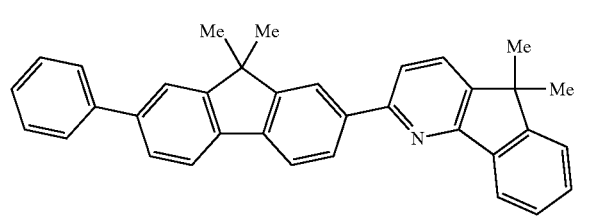

105

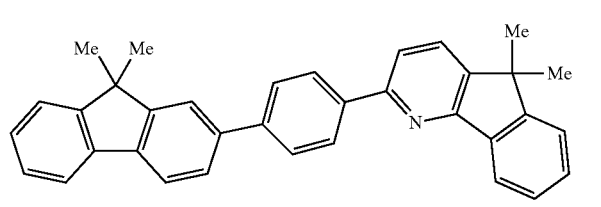

106

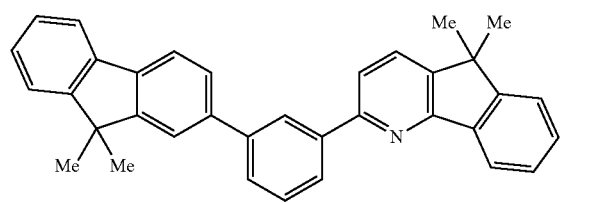

107

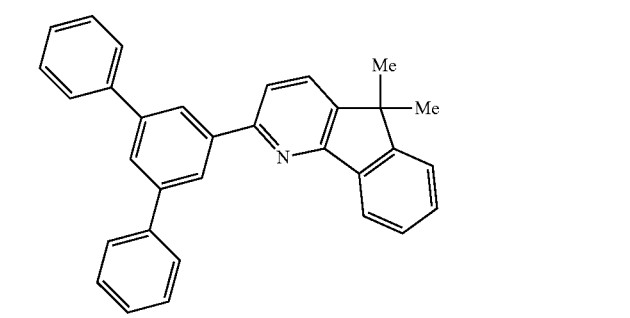

108

-continued
109 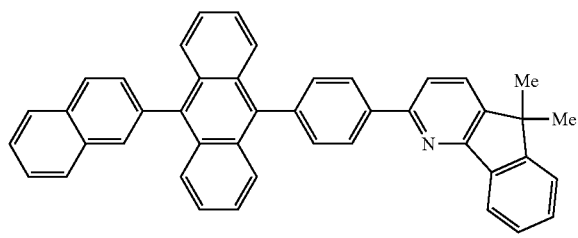
110 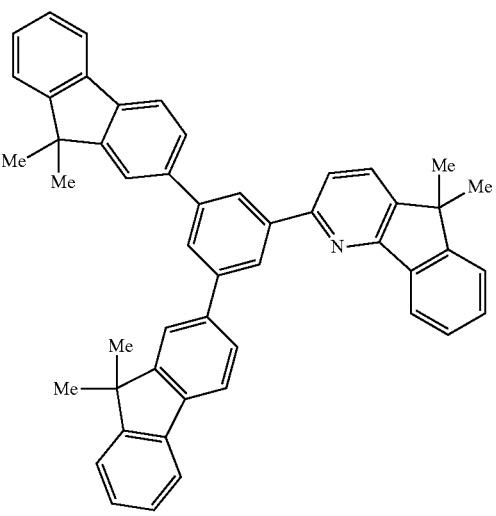
111 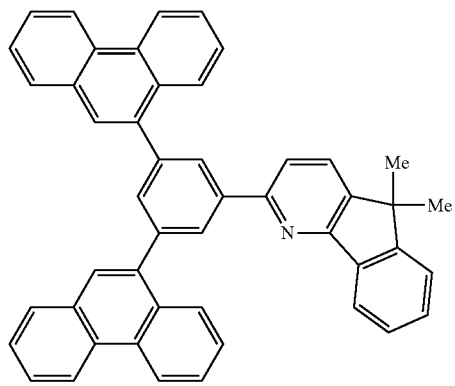
112 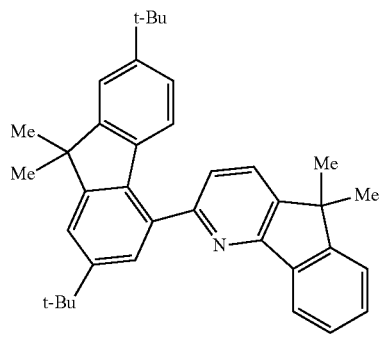
113 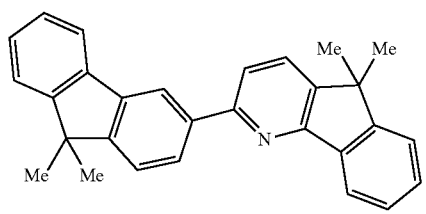
114 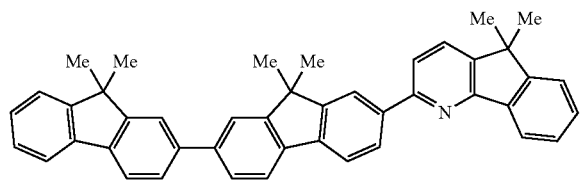
115 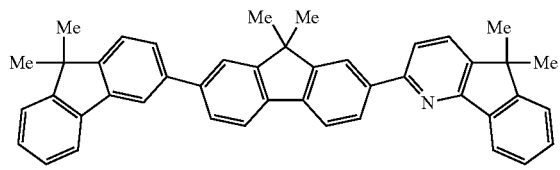
116 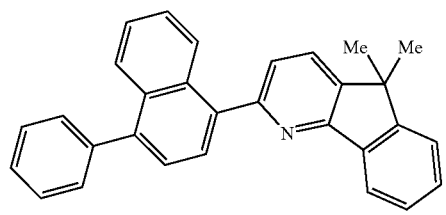
117 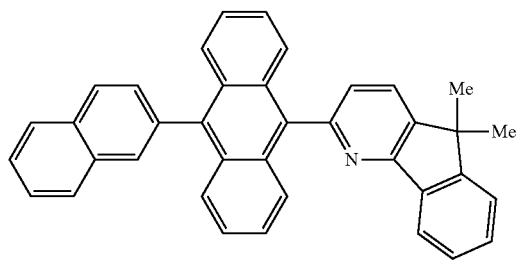
118 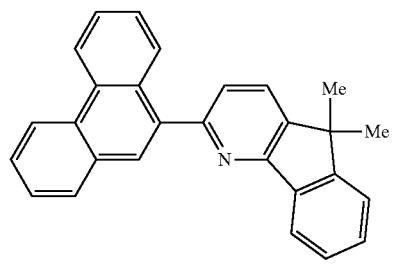

-continued
119 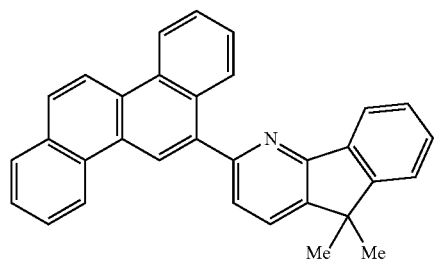
120 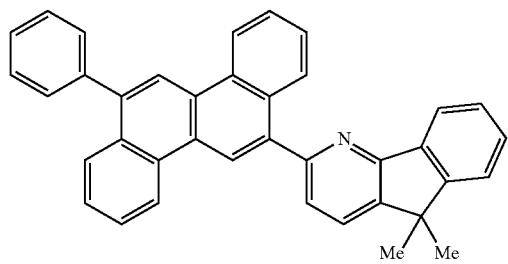
121 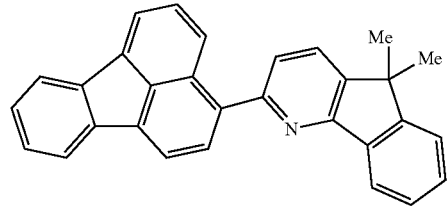
122 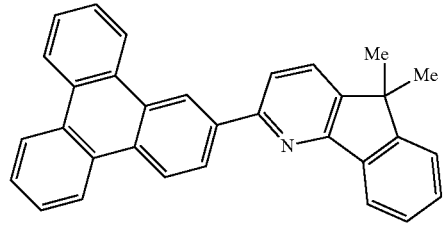
123 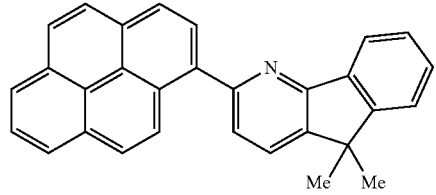
124 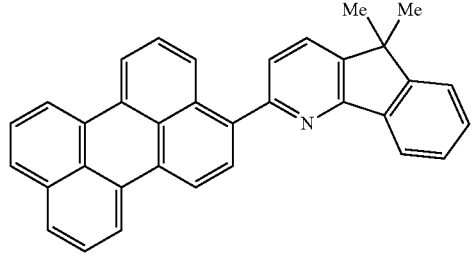
125 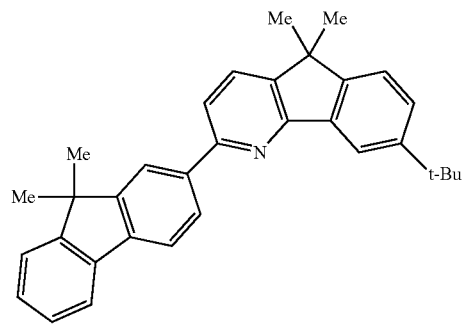
126 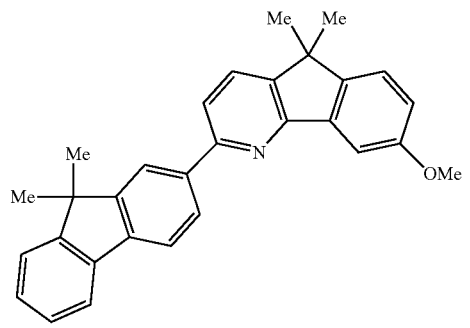
127 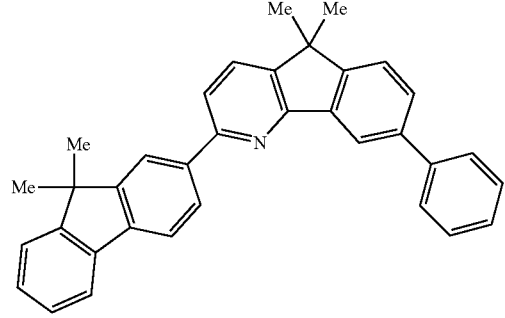
128 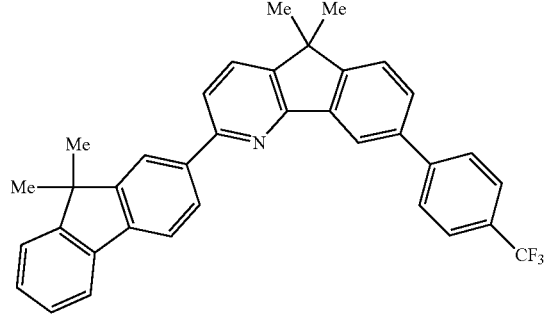

-continued
129
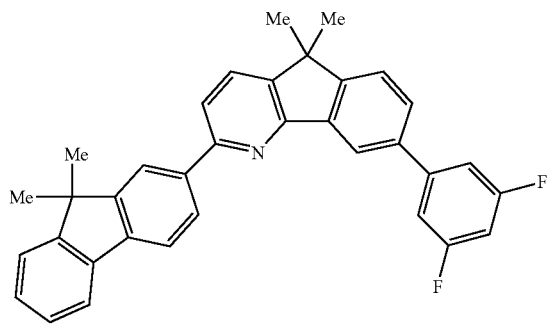
130
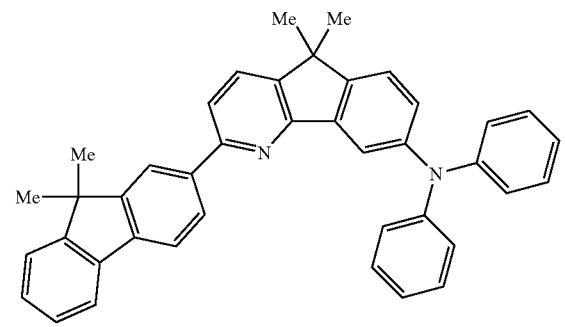
131
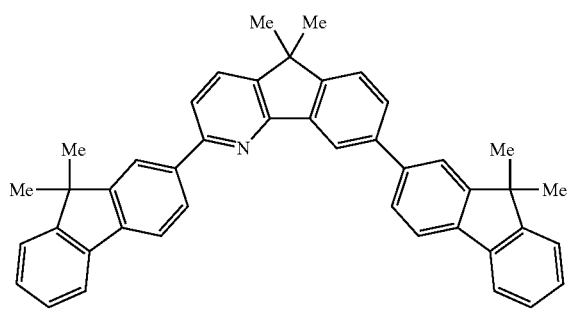
132
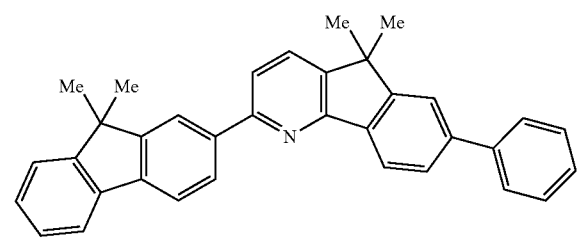
133
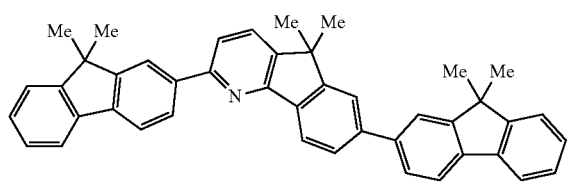
134
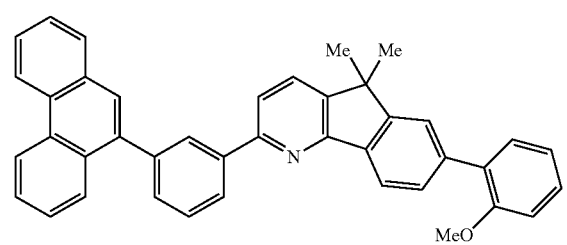
135
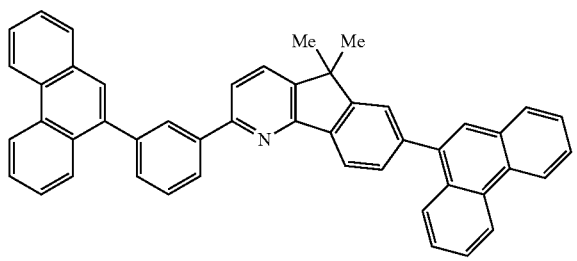
136
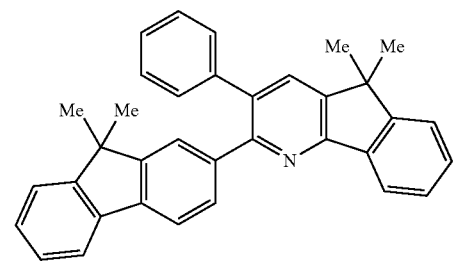
201
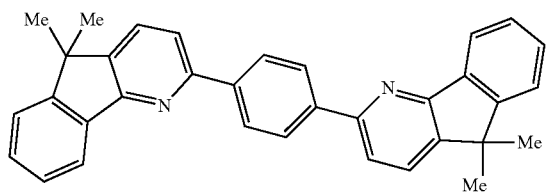
202
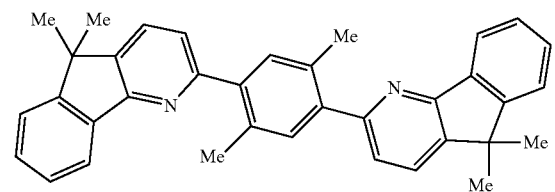

-continued
203 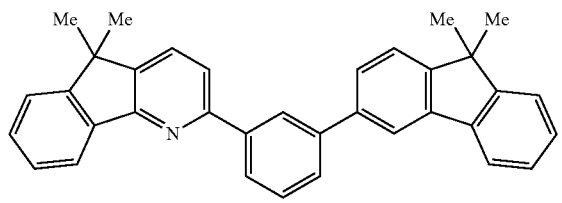
204 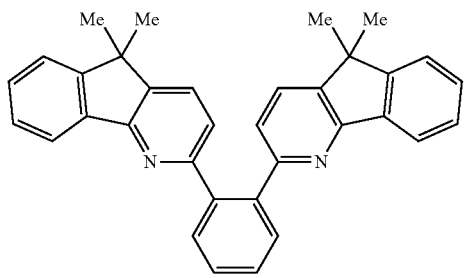
205 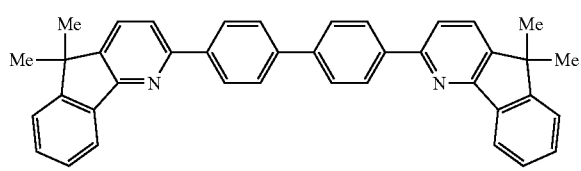
206 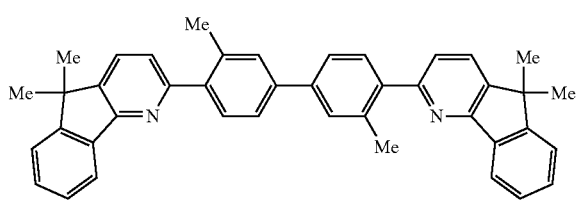
207 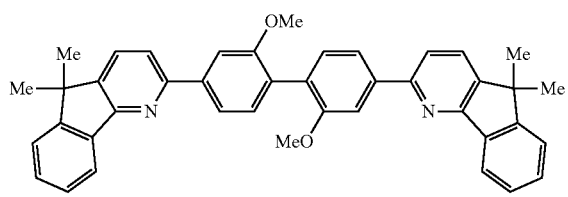
208 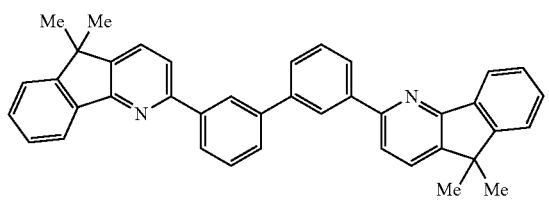
209 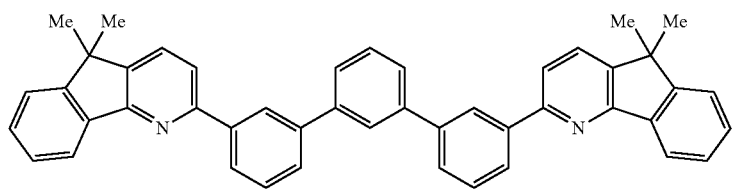
210 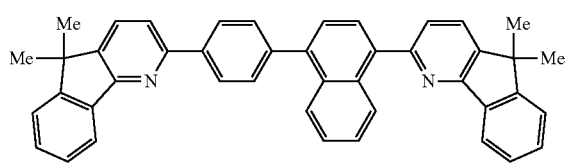
211 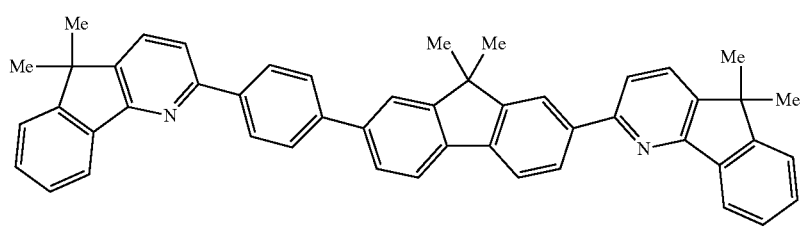
212 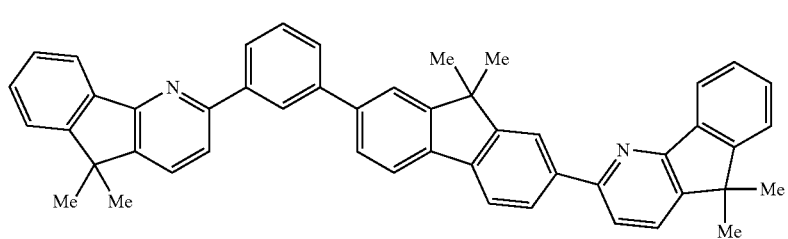

-continued
213
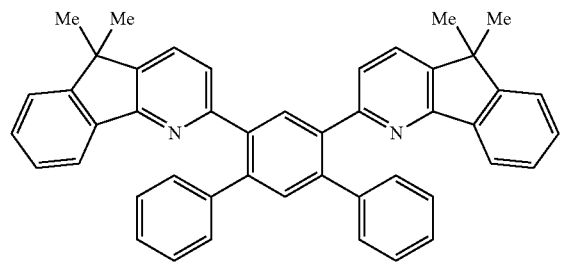
214
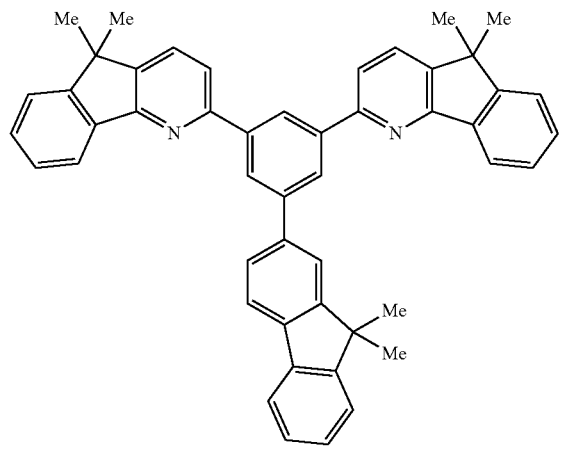
215
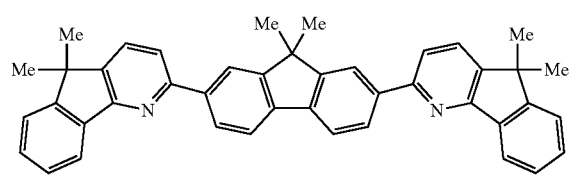
216
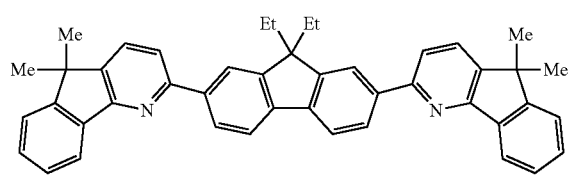
217
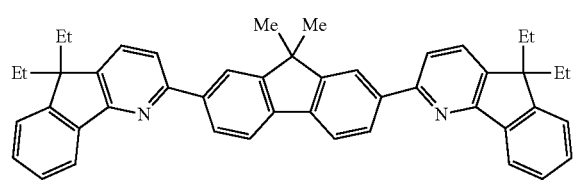
218
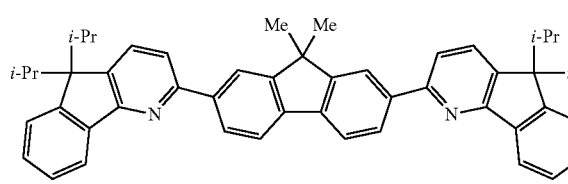
219
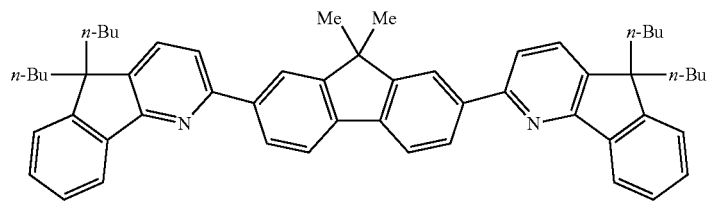
220
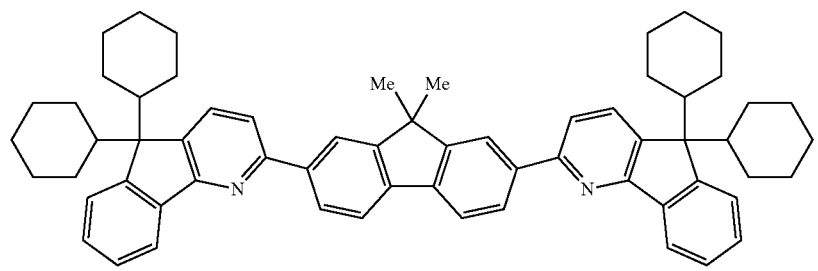
221
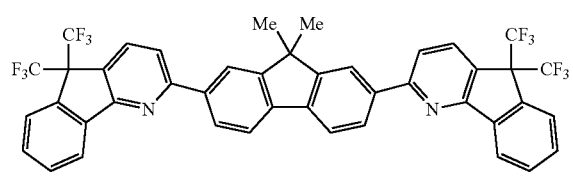
222
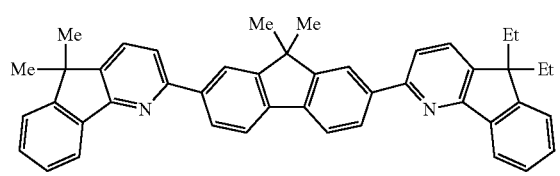

-continued
223
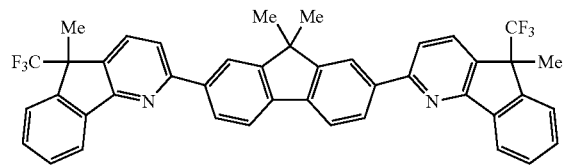
224
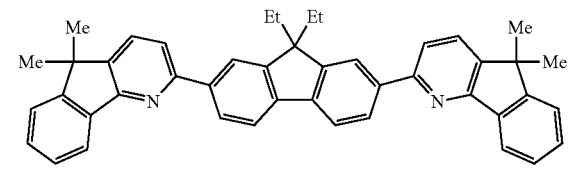
225
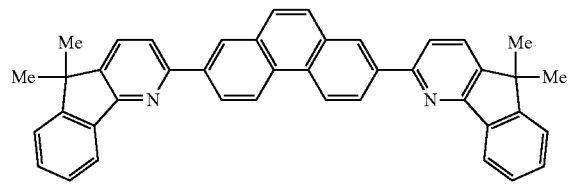
226
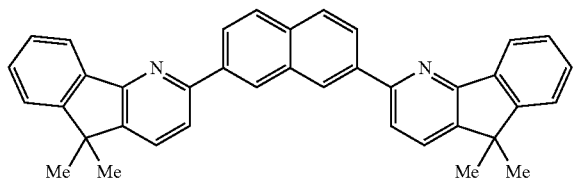
227
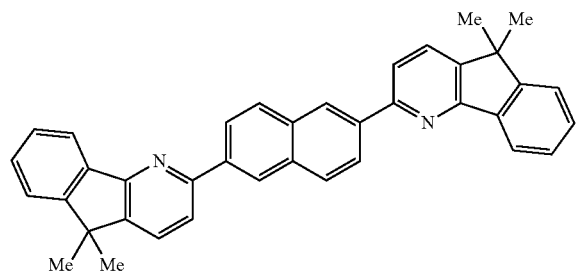
228
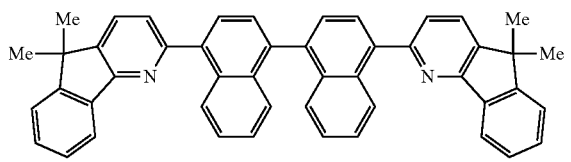
229
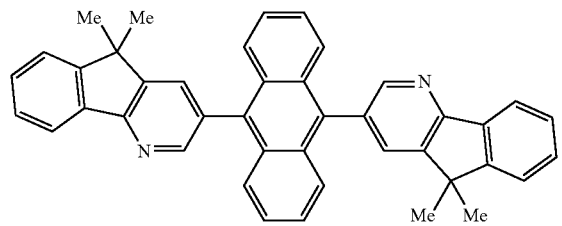
230
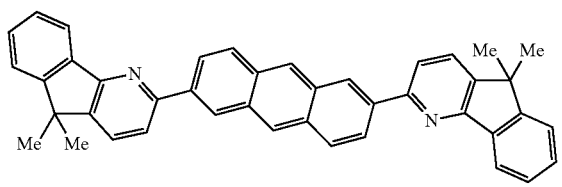
231
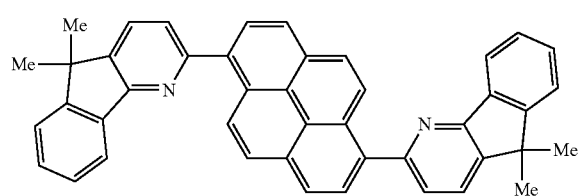
232
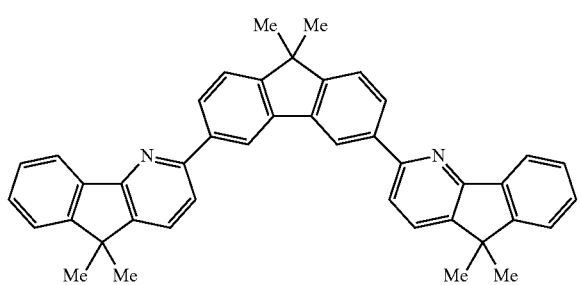
233
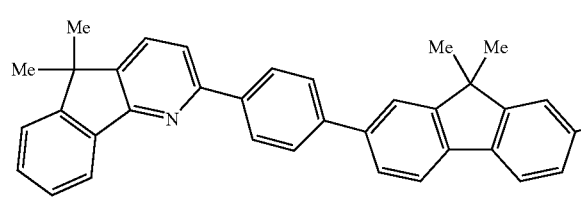

-continued
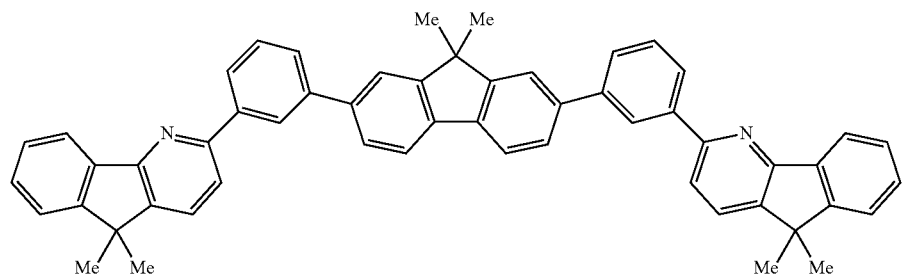
234
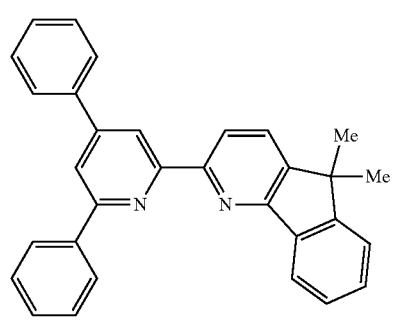
301
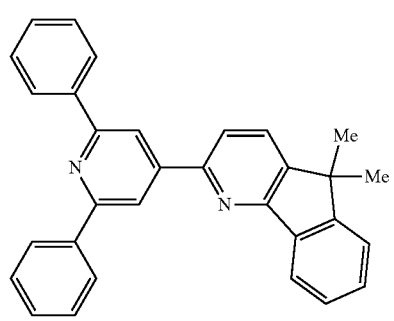
302
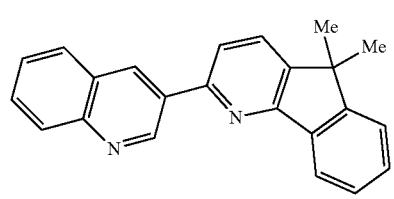
303
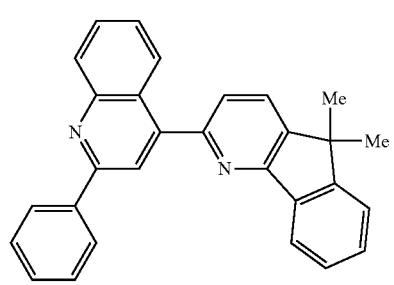
304
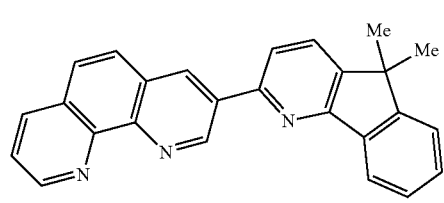
305
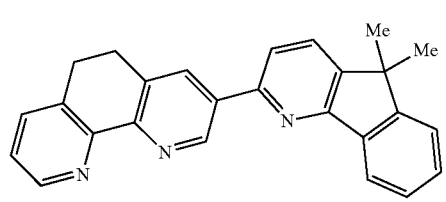
306
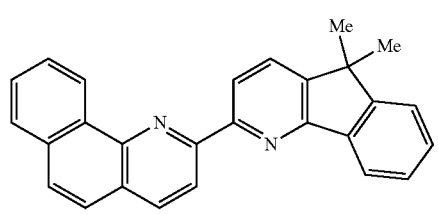
307
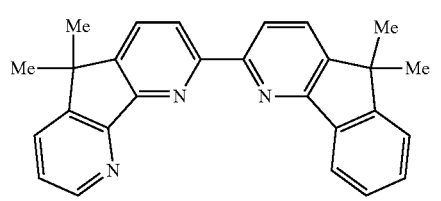
308
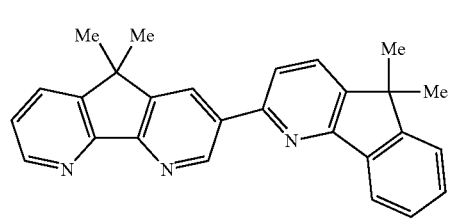
309
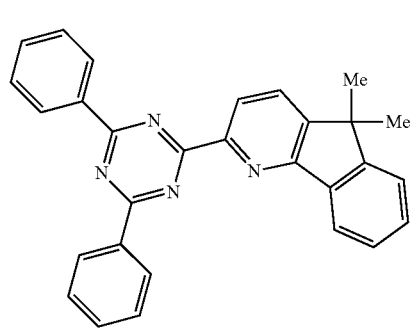
310

-continued
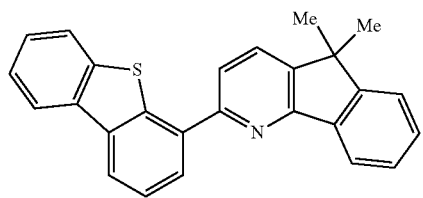
311
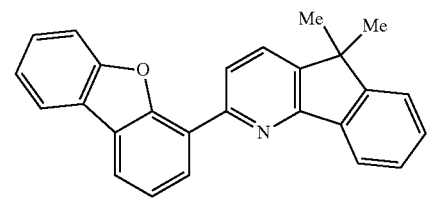
312
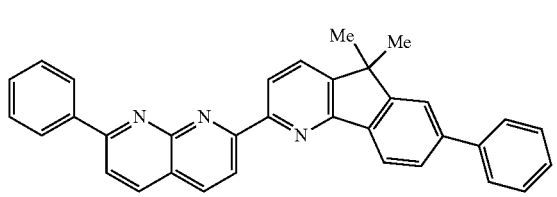
313
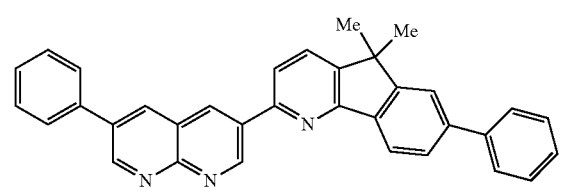
314
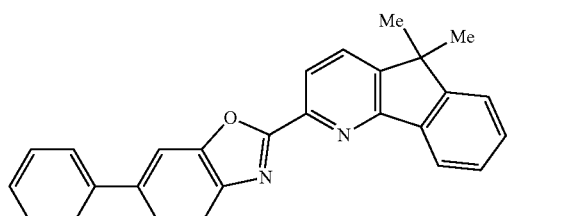
315
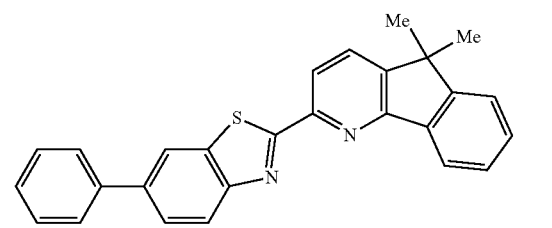
316
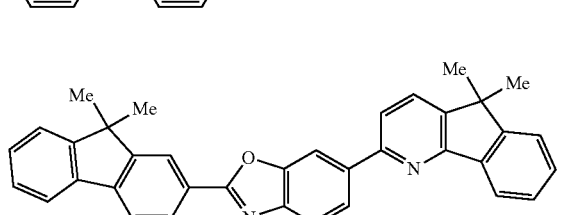
317
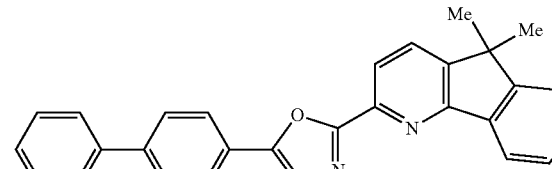
318
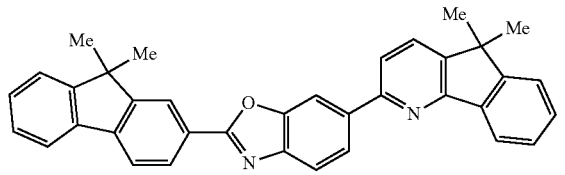
319
320
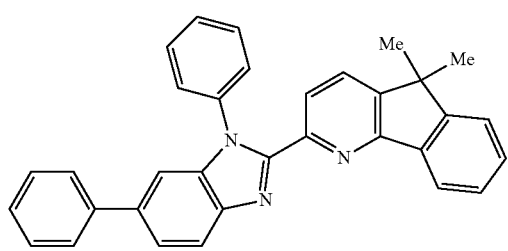
321
322
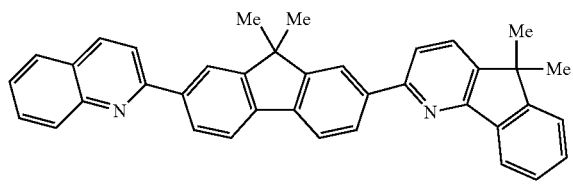
323
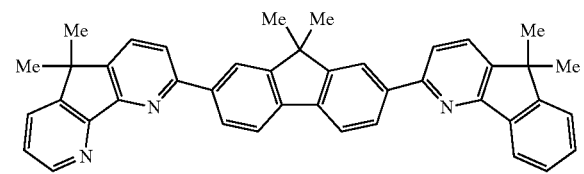
324

-continued
401
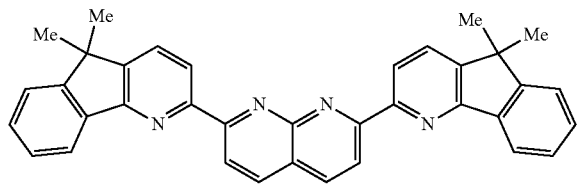
402
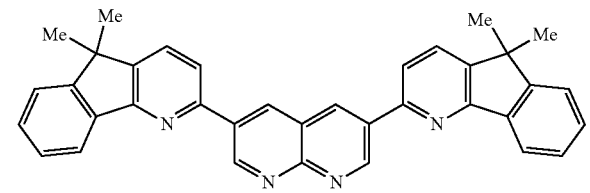
403
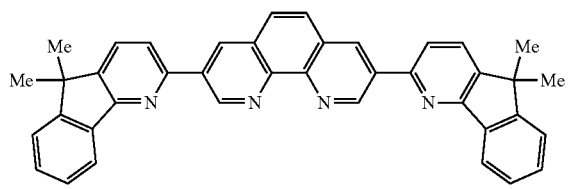
404
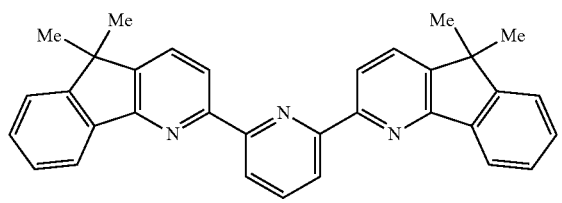
405
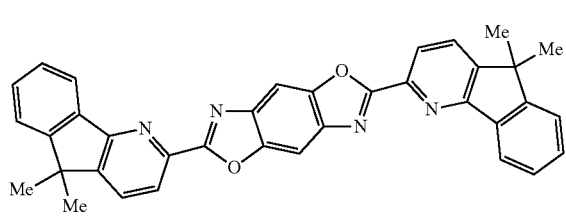
406
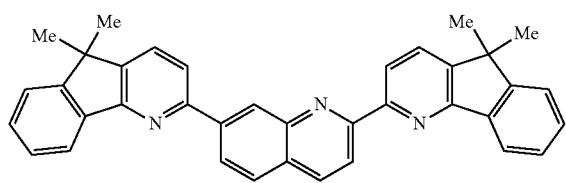
407
408
409
410
501
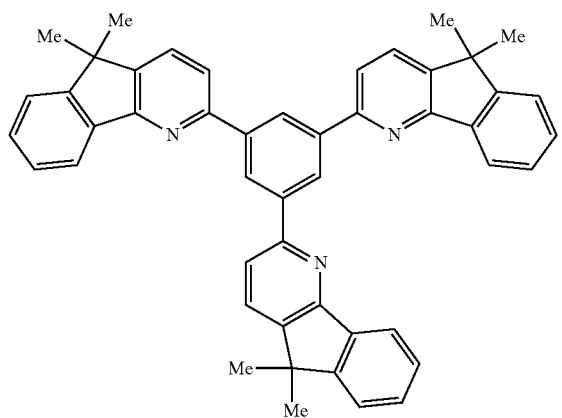
502
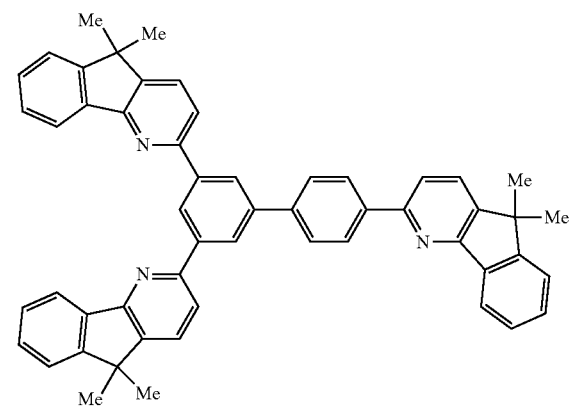

-continued
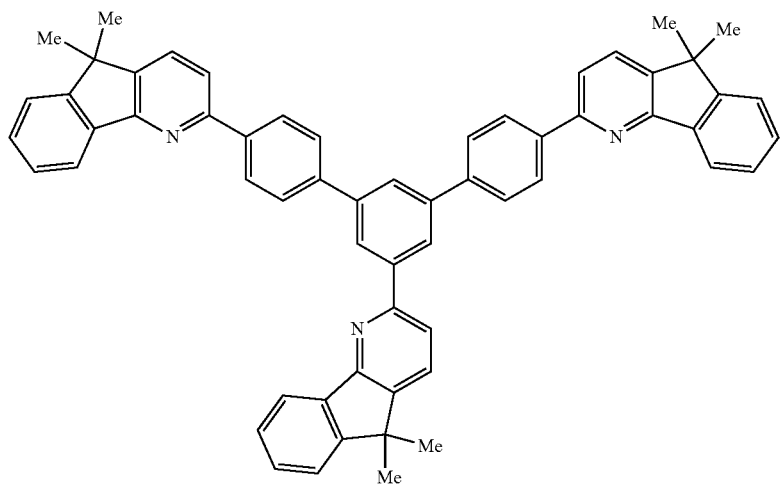
503
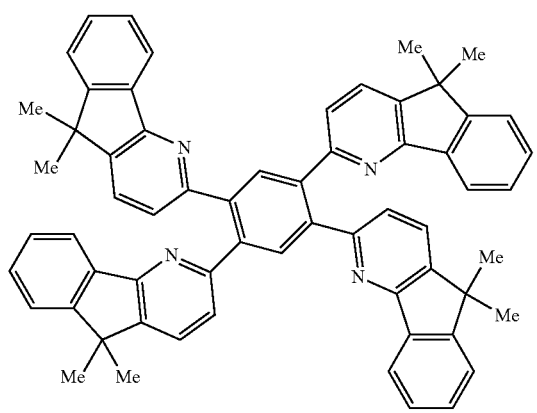
504
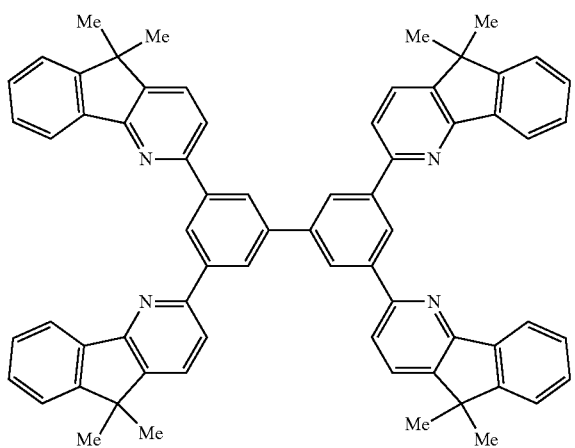
505
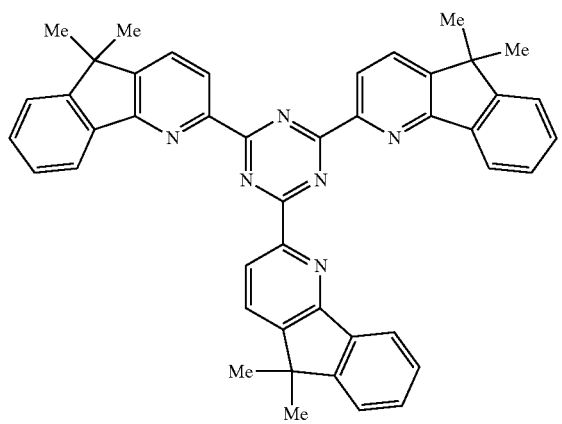
506
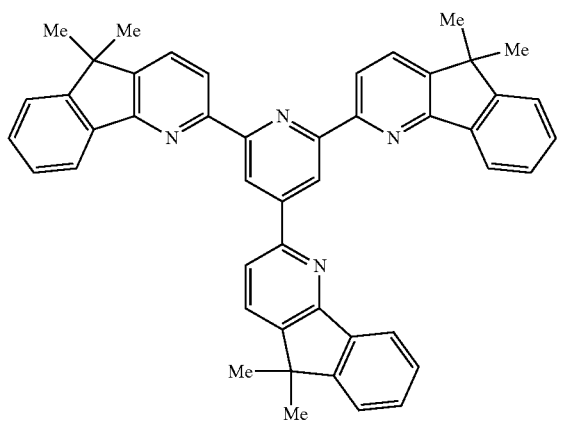
507

-continued
508
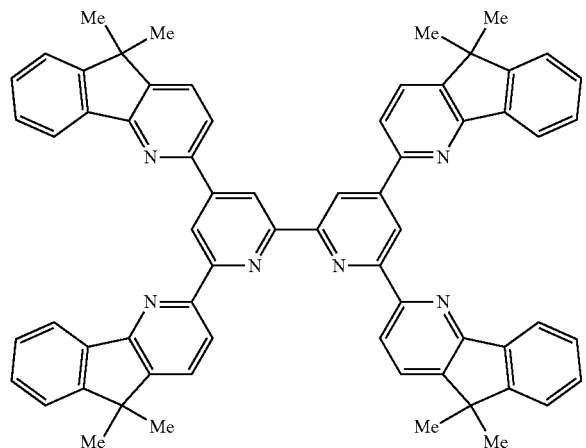
601
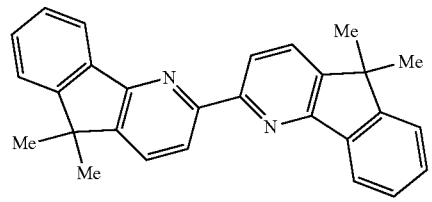
602
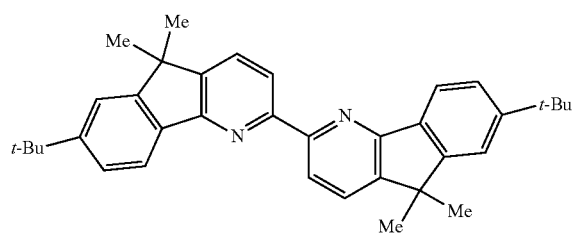
603
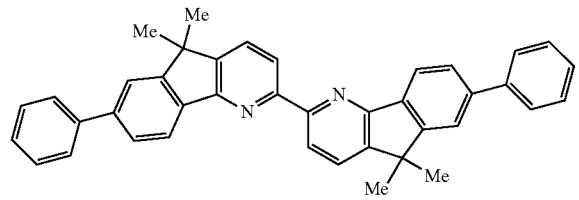
604
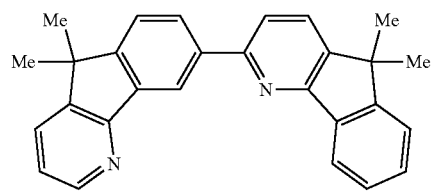
605
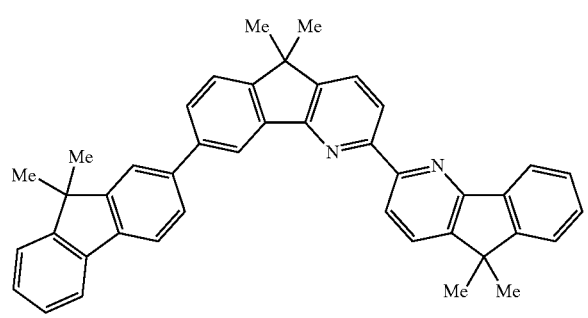
606
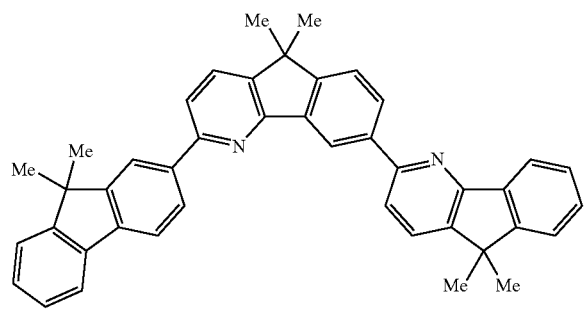
607
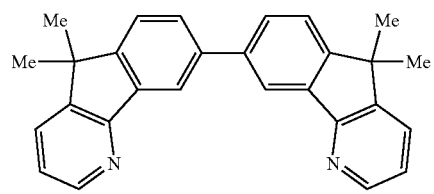

-continued
608
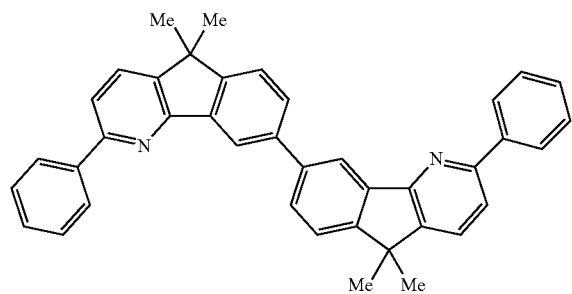
609
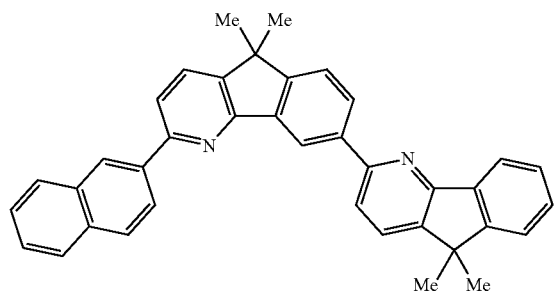
610
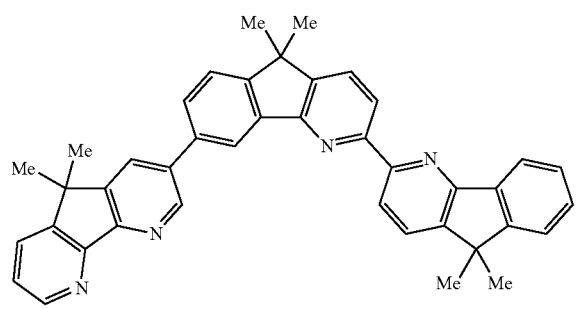
611
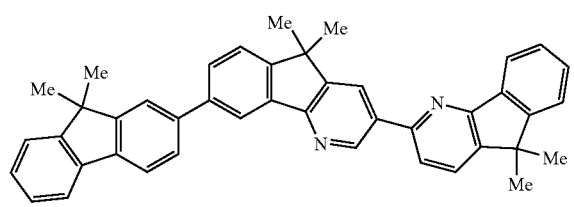
612
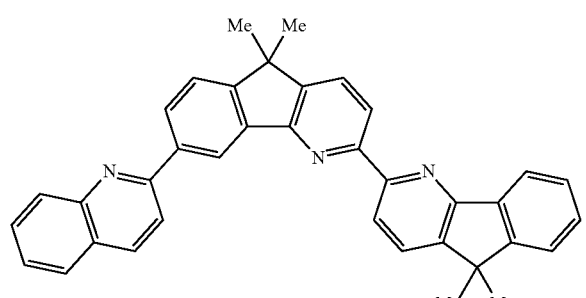
613
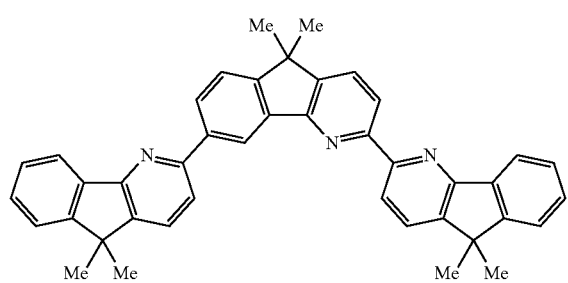
614
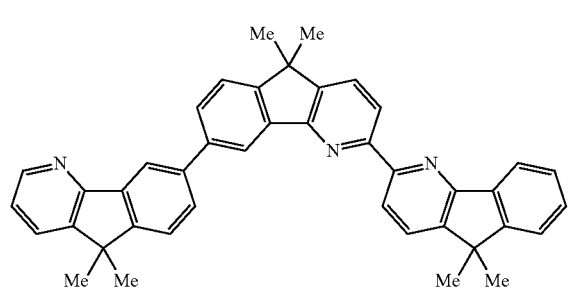
615
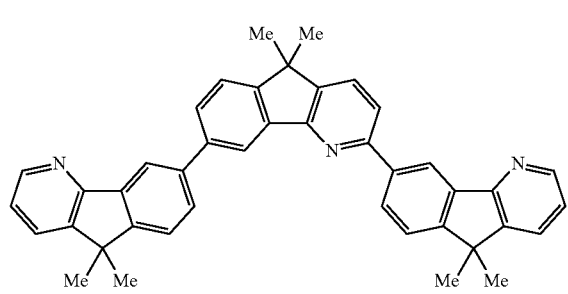
616
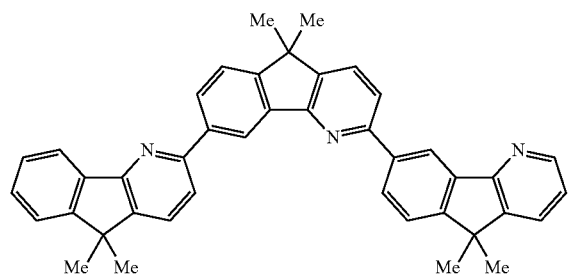

-continued
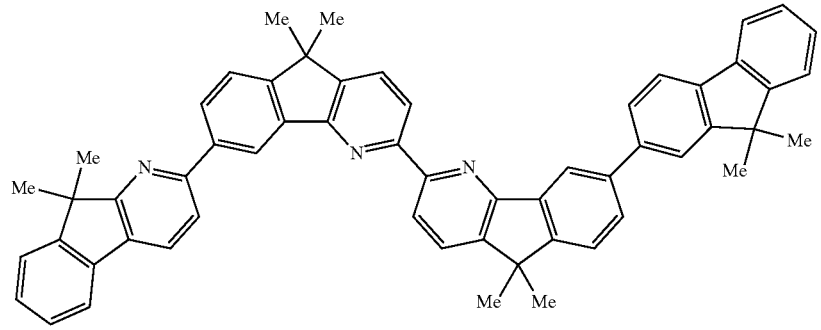
617
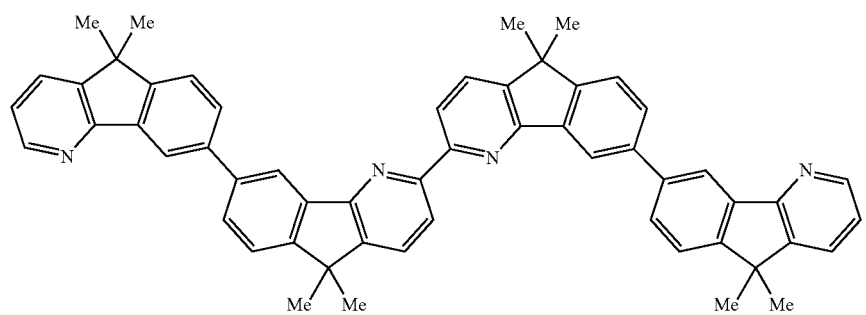
618
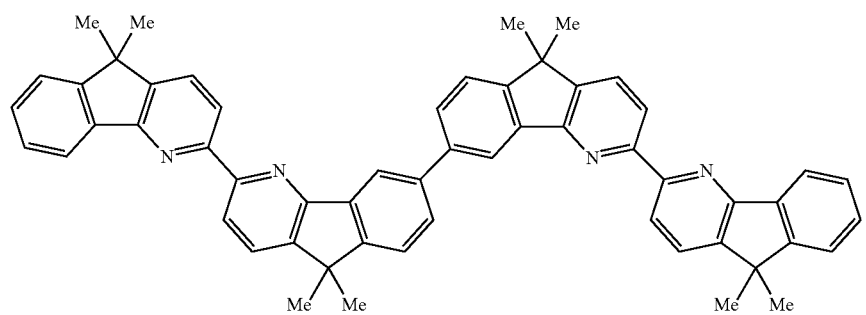
619
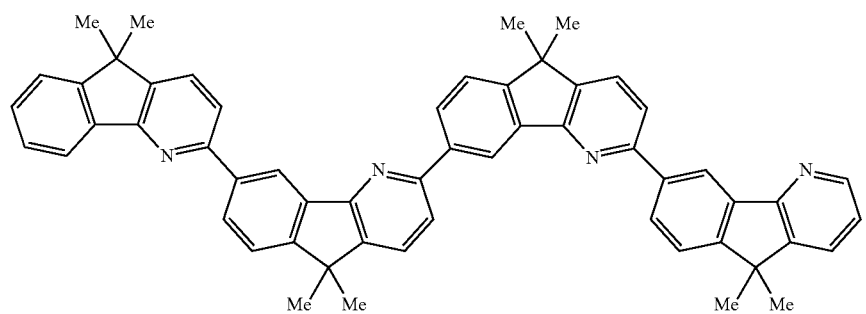
620
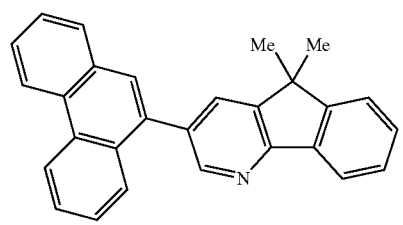
701
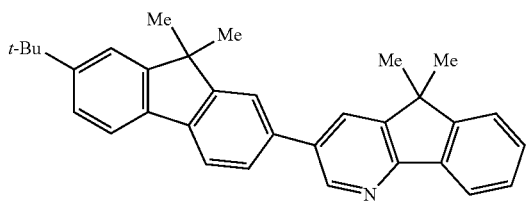
702

-continued
703
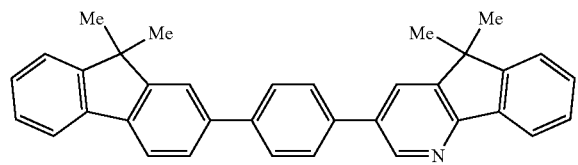
704
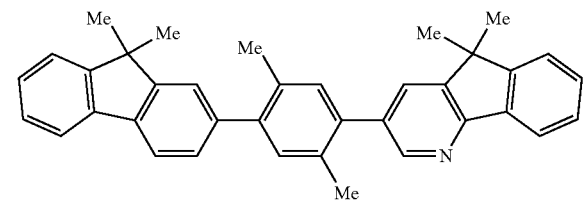
705
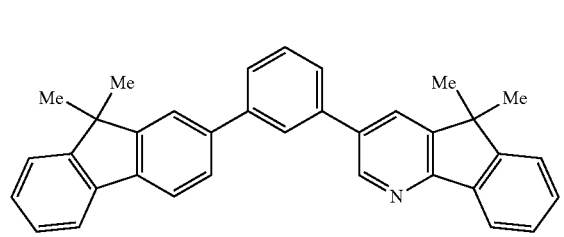
706
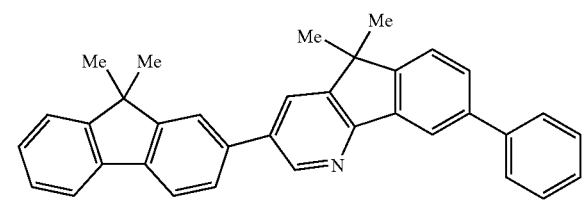
707
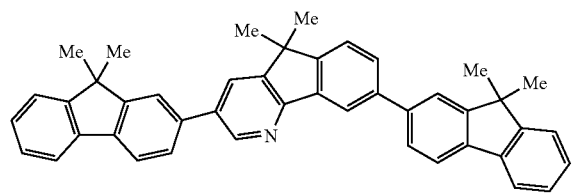
708
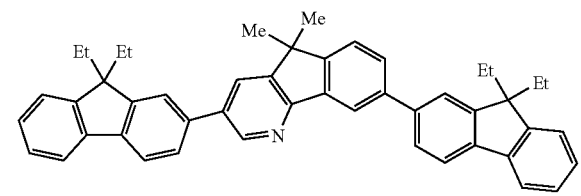
709
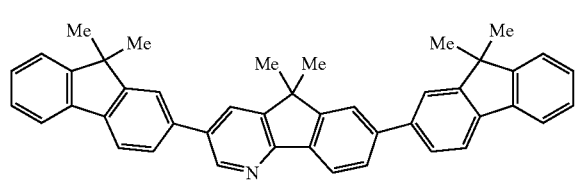
710
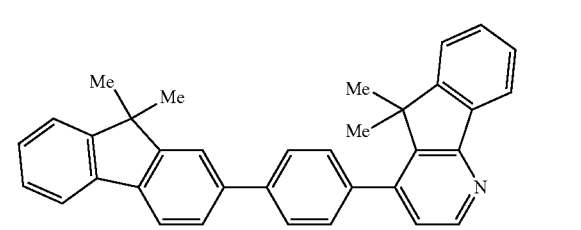
711
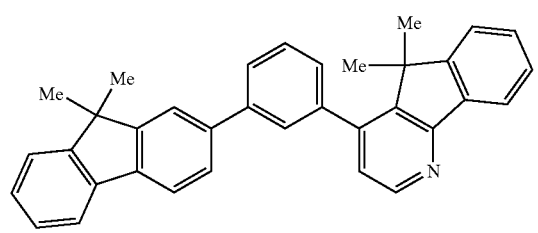
712
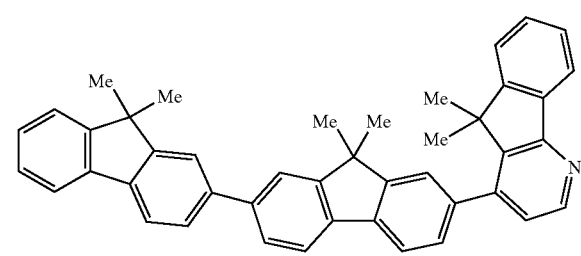
713
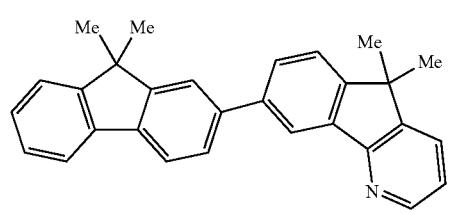
714
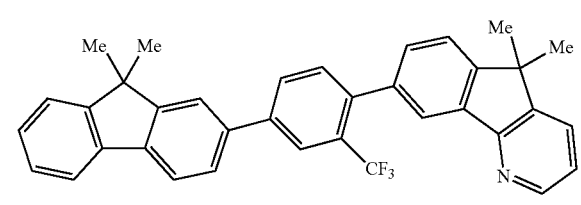

715 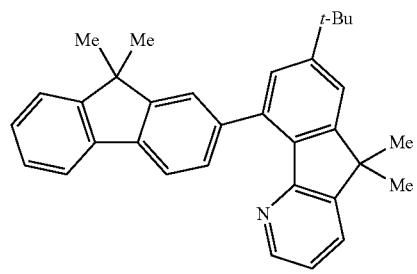 716 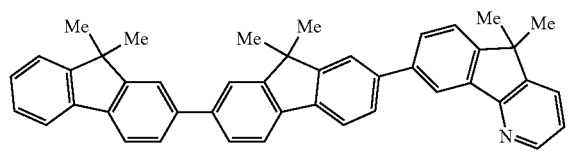
717 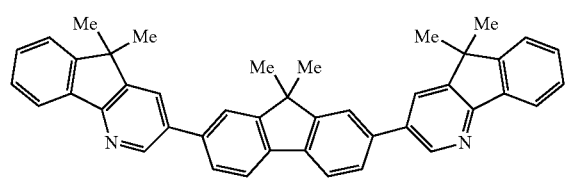 718 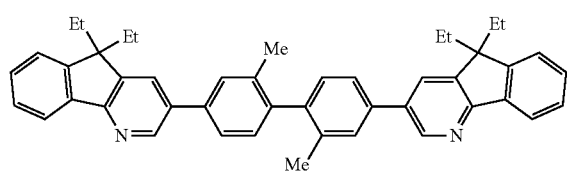
719 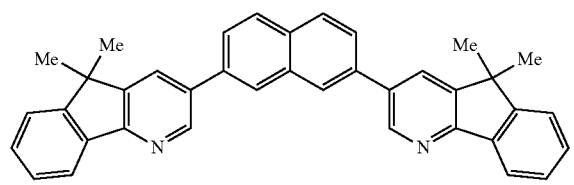 720 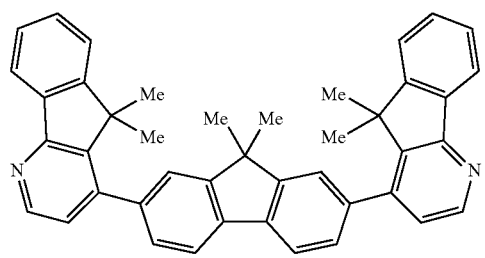
721 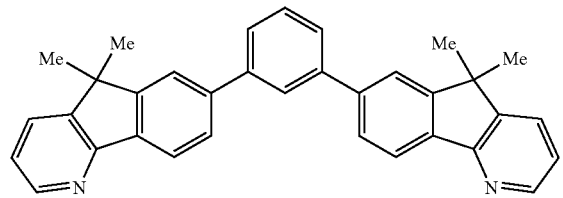 722 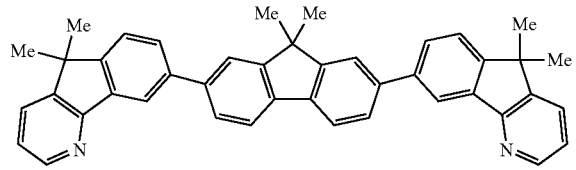
723 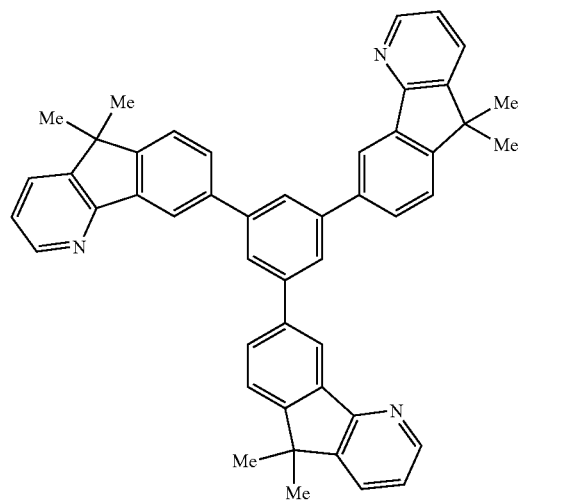 724 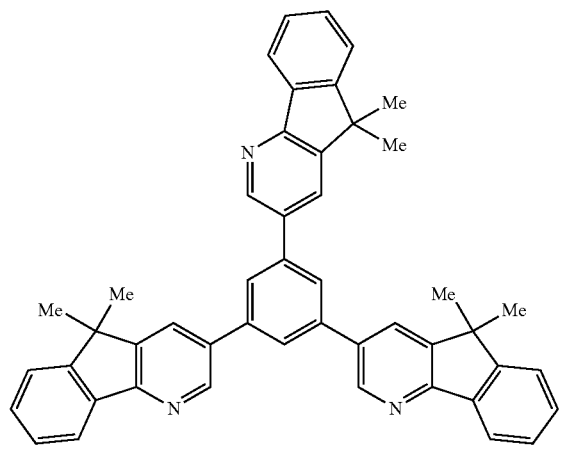

-continued
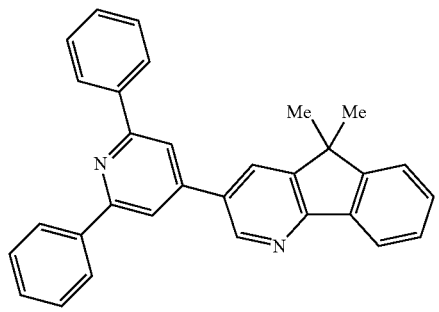 801
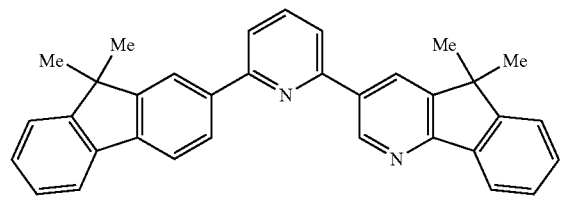 802
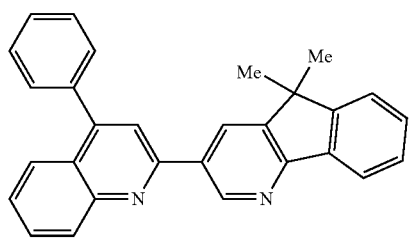 803
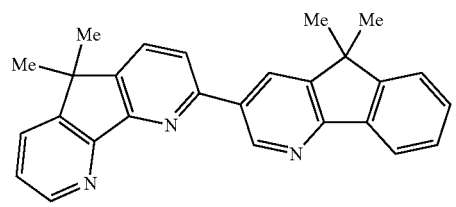 804
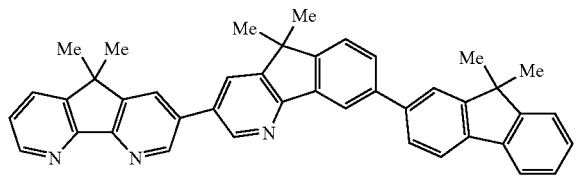 805
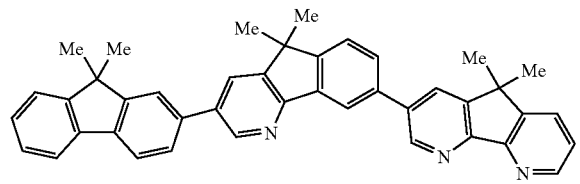 806
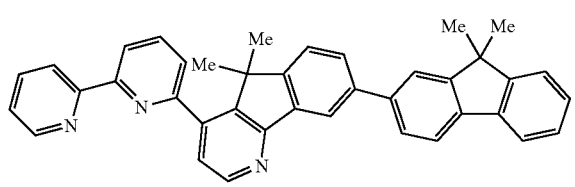 807
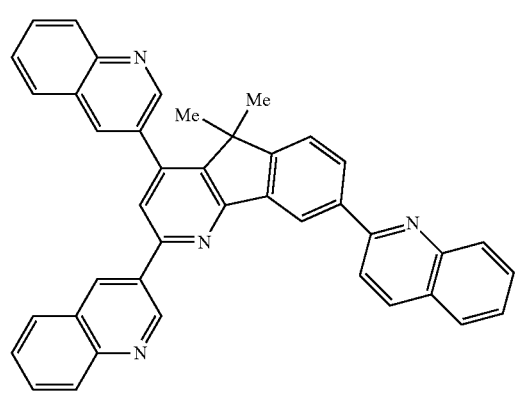 808
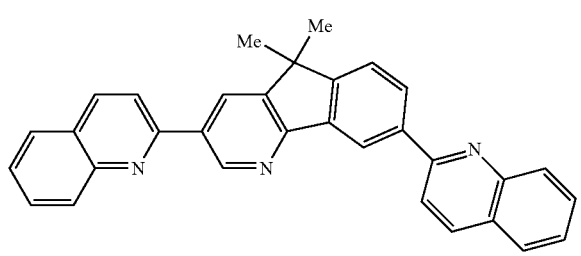 809
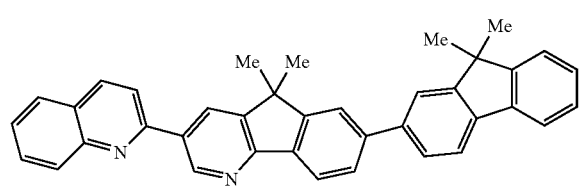 810

-continued
811 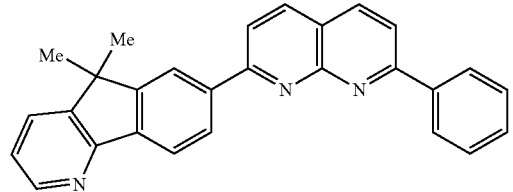
812 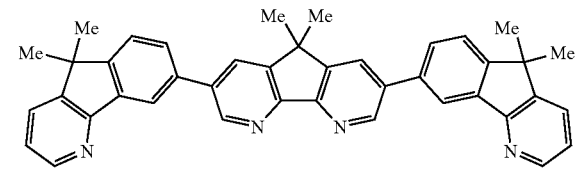
813 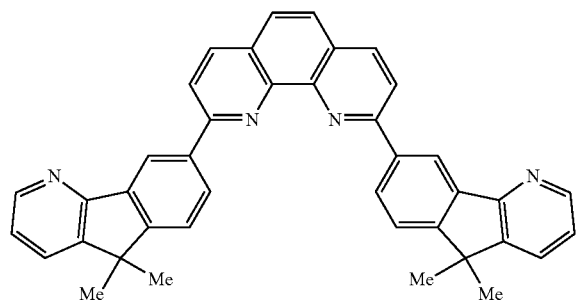
814 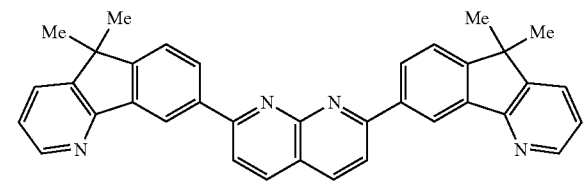
815 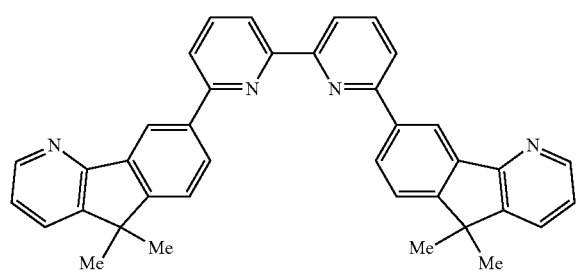
816 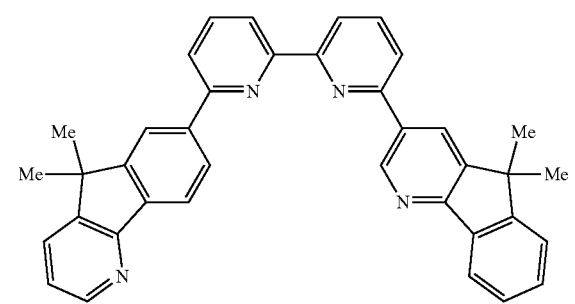
817 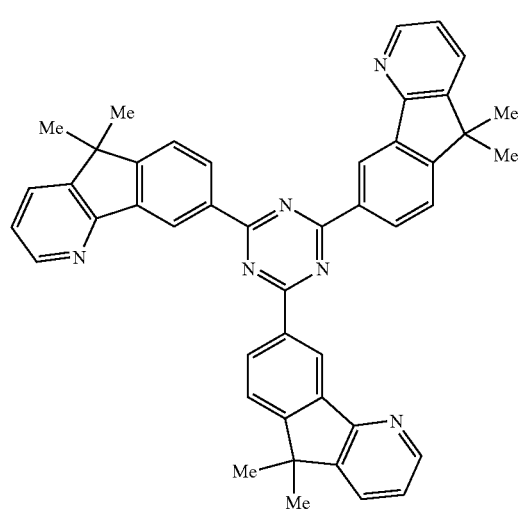
818 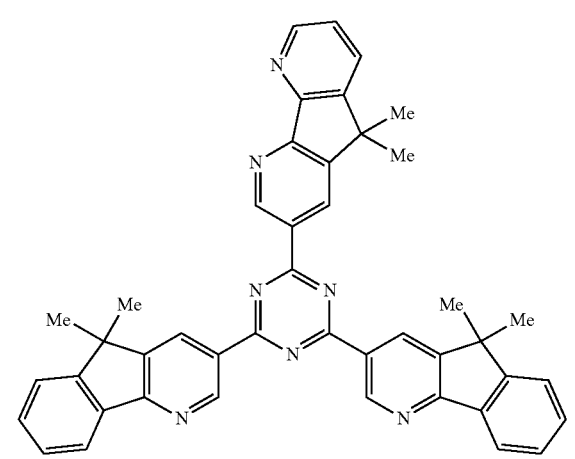
901 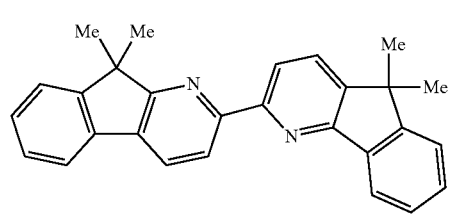
902 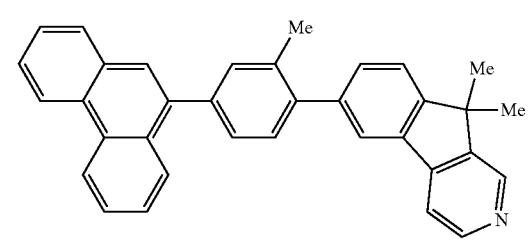

-continued
903
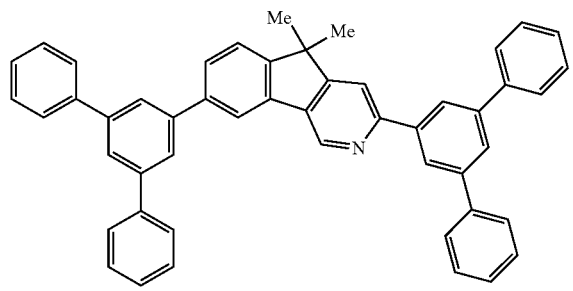
904
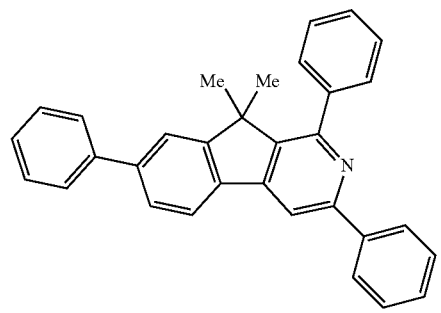
905
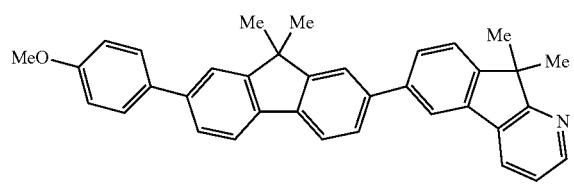
906
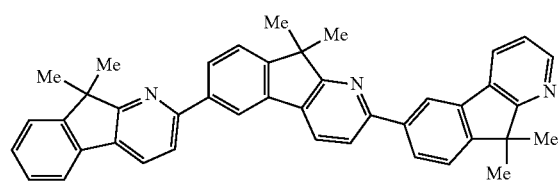
907
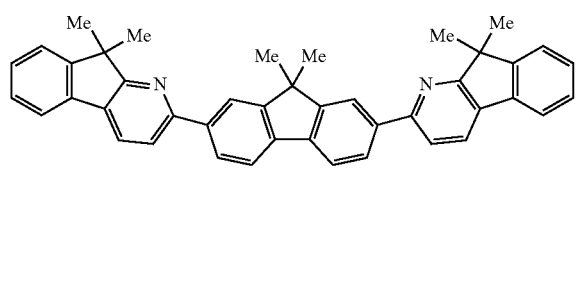
908
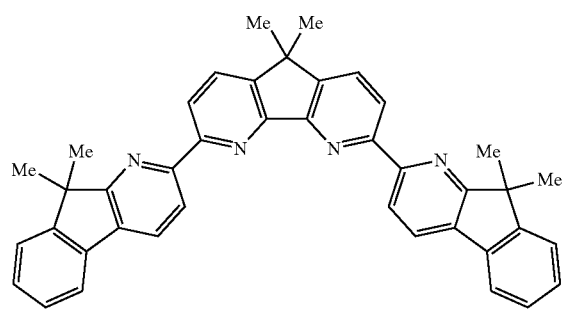
909
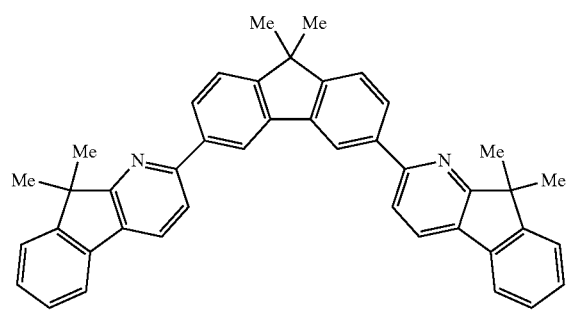
910
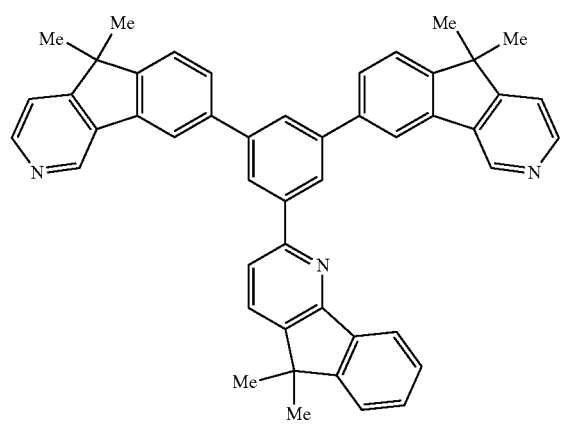

-continued
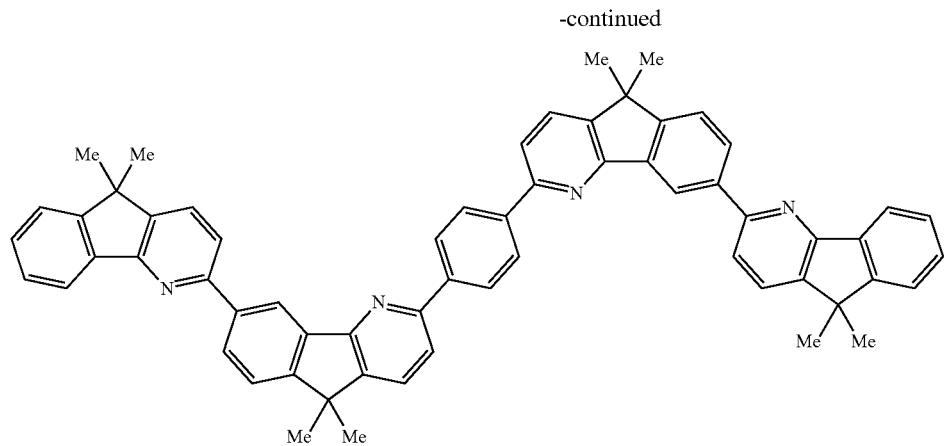
911
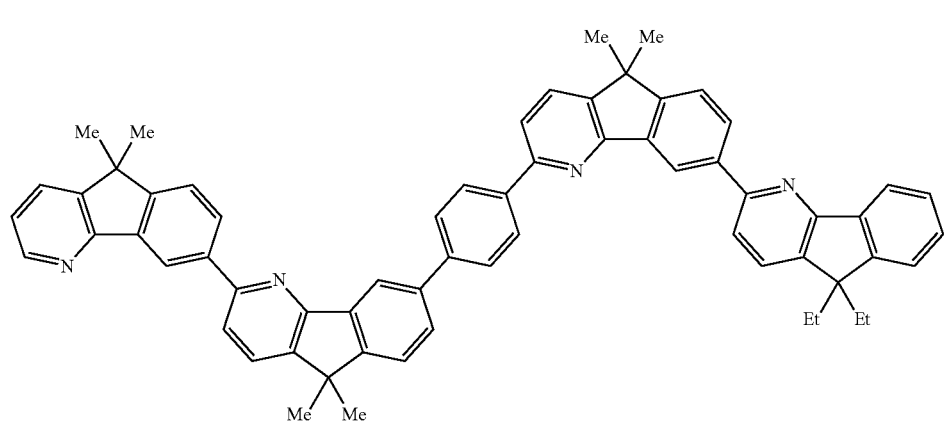
912
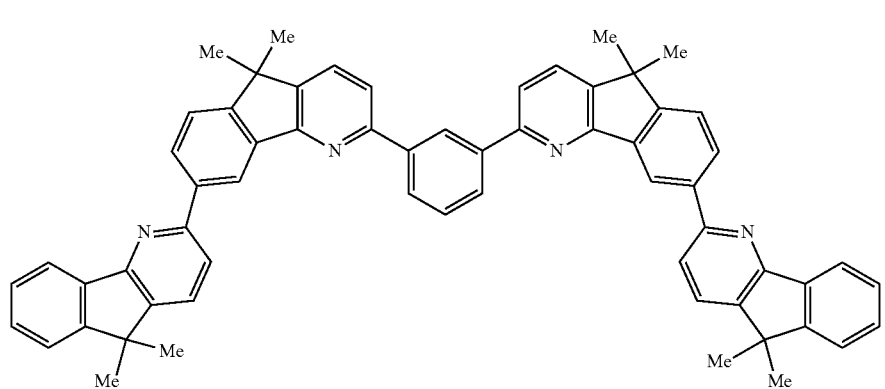
913
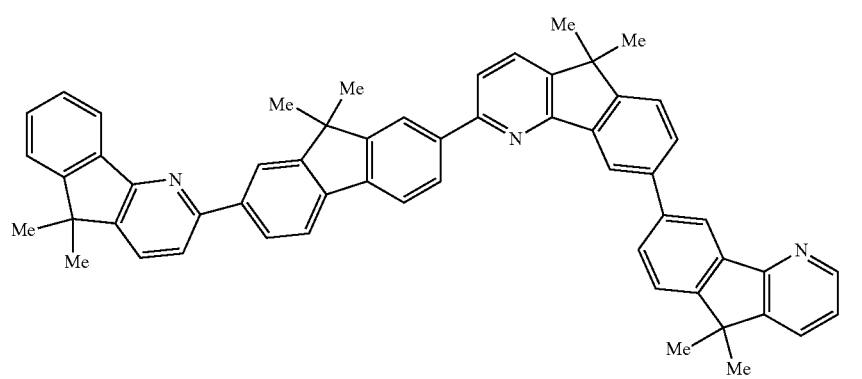
914

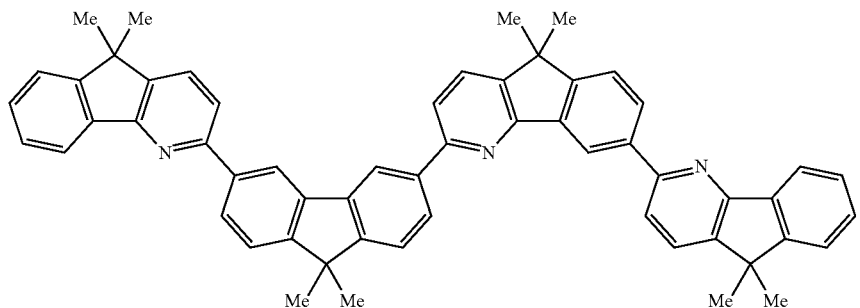

915

Next, the organic light-emitting device of the present invention will be described in detail.

The organic light-emitting device of the present invention includes a pair of electrodes composed of an anode and a cathode and at least one layer interposed between the pair of electrodes, containing an organic compound, either the anode or the cathode being transparent or semi-transparent electrode. In addition, the organic light-emitting device of the present invention contains at least one type of material for the organic light-emitting device of the present invention in the layer containing an organic compound. The organic light-emitting device of the present invention is preferably an electroluminescence device that emits light by applying a voltage between a pair of electrodes.

Hereinafter, the organic light-emitting device of the present invention will be described in detail with reference to the drawings.

FIG. 1 is a sectional view illustrating the first embodiment of the organic light-emitting device according to the present invention. The organic light-emitting device 10 in FIG. 1 includes an anode 2, an organic light-emitting layer 3 and a cathode 4, which are sequentially formed on a substrate 1. The organic light-emitting device 10 is useful in a case where the light-emitting layer 3 is formed form a compound which has all the properties including a hole transporting ability, an electron transporting ability and a light emitting property or a case where the light-emitting layer 3 is formed from a mixture of compounds each having one of a hole transporting ability, an electron transporting ability and a light emitting property.

Figure 2:
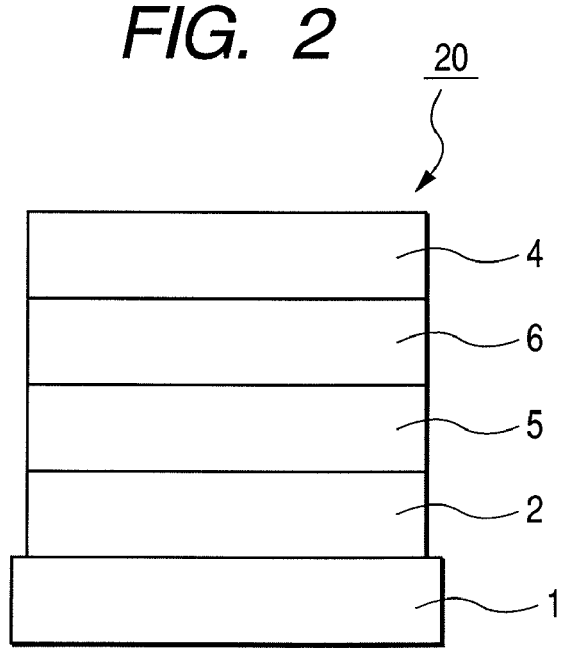
FIG. 2 is a sectional view showing the second embodiment of the organic light-emitting device of the present invention.

FIG. 2 is a sectional view illustrating the second embodiment of the organic light-emitting device according to the present invention. An organic light-emitting device 20 of FIG. 2 includes an anode 2, a hole transport layer 5, an electron transport layer 6 and a cathode 4, which are sequentially formed on a substrate 1. The organic light-emitting device 20 is useful in a case where a light emitting compound having a hole transporting property and/or electron transporting property and an organic compound having only an electron transporting property or only a hole transporting property are used in combination. In addition, in the light-emitting layer 20, the hole transport layer 5 or the electron transport layer 6 serves as the light-emitting layer.

Figure 3:
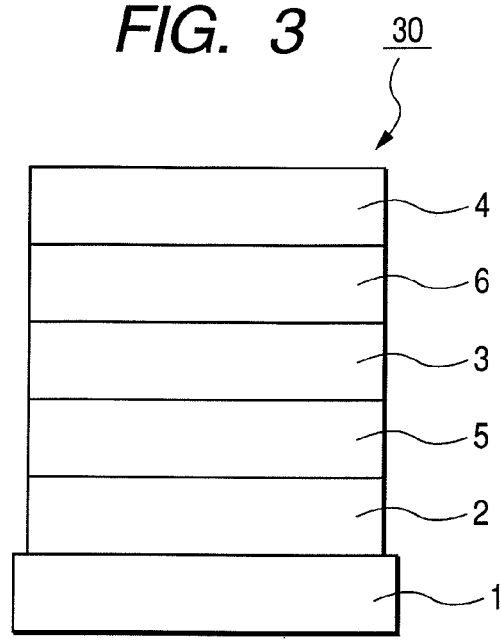
FIG. 3 is a sectional view showing the third embodiment of the organic light-emitting device of the present invention.

FIG. 3 is a sectional view illustrating the third embodiment of the organic light-emitting device according to the present invention. An organic light-emitting device 30 of FIG. 3 illustrate a structure in which the light-emitting layer 3 is inserted between a hole transport layer 5 and an electron transport layer 6 in the organic light-emitting device 30 of FIG. 2. In the organic light-emitting device 30, a carrier-transporting function and a light-emitting function are separated from each other. Thus, the device can be used appropriately in combination with compounds each having one of a hole-transporting property, electron transporting property and light emitting property. Therefore, the degree of freedom of material selection extremely increases, and additionally, since various compounds different from each other in emission wavelength can be used, luminescent hues can be diversified. Further, the emission efficiency of the organic light-emitting device 30 can be improved by effectively trapping carriers or excitons in the light-emitting layer 3.

Further, in FIG. 3, a hole injection layer may be inserted between the anode 2 and the hole transport layer 5. The insertion of the hole injection layer in the organic light-emitting device improves the adhesiveness between the anode 2 and the hole transport layer 5, or the hole injection property, and hence, is effective in reducing voltage at which the device is driven.

Further, in FIG. 3, a layer for inhibiting holes or excitons escaping through the side of the cathode 4 (hole blocking layer/exciton blocking layer) may be inserted between the light-emitting layer 3 and the electron transport layer 6. A compound having high ionization potential is used as the hole blocking layer/exciton blocking layer to improve the emission efficiency of the organic light-emitting device.

It should be noted that FIGS. 1 to 3 merely illustrate very basic device structures, and the structure of the organic light-emitting device of the present invention is not limited thereto. For example, it is possible to adopt various layer structures as follows: an insulating layer, an adhesive layer or an interference layer is provided to the interface between an electrode and an organic layer; and a hole transport layer is composed of two layers different in ionization potential.

At least one type of material for the organic light-emitting device of the present invention is contained in a layer formed from an organic compound such as the light-emitting layer 3, the hole transport layer 5, or the electron transport layer 6 shown in FIGS. 1 to 3. The material is incorporated into preferably the hole-blocking layer, the electron transport layer or an electron injection layer, or particularly preferably the electron transport layer.

In general, when a layer having an electron transport property is provided between the light-emitting layer and cathode of an organic light-emitting device, the following four functions are primarily required for the layer having an electron transport property. The layer is referred to as an electron injection layer, an electron transport layer, an exciton-blocking layer or a hole-blocking layer for each function.
(1) Receiving electrons injected from the cathode (electron injection).
(2) Transporting electrons to the light-emitting layer (electron transport).

(3) Blocking the escape of excitons from the light-emitting layer (exciton block)
(4) Blocking the leakage of holes from the light-emitting layer (hole block)

An electron transport layer formed from a single electron transport material may be provided with those functions. Alternatively, a laminated structure may be composed of multiple layers formed from materials different in function such as an electron transport layer and an electron injection layer.

It is known that a heteroaromatic ring derivative typified by an oxadiazole derivative, a quinoline derivative or a phenanthroline derivative is generally preferable as an electron transport material in terms of the above-mentioned functions of the electron transport layer. However, an organic light-emitting device using any one of such electron transport materials in its electron transport layer still involves a large number of problems concerning the voltage at which the device is driven, emission efficiency and durability. Therefore, when using the azaphenanthrene derivative of the present invention, these problems can be solved.

In an organic layer containing the material for the organic light-emitting device of the present invention, the material for the organic light-emitting device may be used alone, or may be mixed with any other material to form a mixed organic layer. When being used for the mixed organic layer, the content of the material for the organic light-emitting device of the present invention is 0.01 wt % or more and 99.99 wt % or less and preferably 5 wt % or more and 95 wt % or less. Similarly, the material for the organic light-emitting device of the present invention may be mixed with any other inorganic compound to form a mixed layer. For example, it is possible that the azafluorene derivative as the material for the organic light-emitting device of the present invention is doped with an alkali metal to form an electron injection layer between an electron transport layer and a cathode.

In the organic light-emitting device of the present invention, a hole transport (injection) layer, a light-emitting layer, an electron transport (injection) layer, etc. can be provided by using conventionally known low- and high-molecular-weight-type materials for an organic light-emitting device together with the material for the organic light-emitting device of the present invention as required.

A material in which holes are easily injected from the anode and which has high hole mobility with which the injected hole is transported to the light-emitting layer is preferably used in the hole transport (injection) layer. Examples of such a hole injection/transport material includes, but is not limited to, a triarylamine derivative, a phenylenediamine derivative, a stilbene derivative, a phthalocyanine derivative, a porphyrin derivative, poly(vinylcarbazole), poly(thiophene), and other conductive polymers.

It is preferable to use in the light-emitting layer a material in which carriers transported and injected from the hole transport layer and the electron transport layer are efficiently recombined to produce excitons and are deactivated by radiation to emit light in a high emission quantum yield. In general, a mixture of a host compound having carrier transport property and a guest compound having light-emitting property is more preferably used because light with high luminance can be emitted with high emission efficiency.

A generally known fluorescent material or phosphorescent material may be used as the above-mentioned guest compound. The concentration of the guest compound with respect to the host compound is in the range of 0.01 wt % to 50 wt % and preferably 1 wt % to 30 wt %. Further, multiple light-emitting materials may be incorporated into the light-emitting layer for the purposes of causing the light-emitting layer to emit light beams having multiple colors and of aiding transfer of excitons or charges. The guest compound may be incorporated into the entirety of the layer formed of the host compound uniformly or with a concentration gradient, or may be partially incorporated into a specific region of the host compound layer so that the layer has a region free of the guest compound.

The material for the organic light-emitting device of the present invention may be used as a guest compound together with any other host compound.

Examples of such a material for the light-emitting layer as described above include, but are not limited to, the following compounds as well as the azafluorene derivative as the material for the organic light-emitting device of the present invention: a fused aromatic ring compound (such as a fluorene derivative, a pyrene derivative, a tetracene derivative, an anthracene derivative, a fluoranthene derivative, a benzofluoranthene derivative, or rubrene), a quinacridone derivative, a coumarin derivative, a stilbene derivative, an organic aluminum complex such as tris(8-quinolinolato)aluminum, an organic beryllium complex, a polymer derivative such as a poly(phenylenevinylene) derivative, a poly(fluorene) derivative or a poly(phenylene) derivative, and a phosphorescent metal complex (such as an iridium complex, a platinum complex, a rhenium complex, a copper complex, a europium complex or a ruthenium complex).

A material in which electrons are easily injected from the cathode and which has an electron transport property of transporting the injected electrons to the light-emitting layer, is preferably used in the electron transport (injection) layer, and the material is selected in consideration of, for example, a balance between the amount of holes to be injected from the hole transport layer into the light-emitting layer and carrier mobility in the light-emitting layer. Examples of such an electron injection/transport material include, but are not limited to, an oxadiazole derivative, an oxazole derivative, a pyrazine derivative, a triazole derivative, a triazine derivative, a quinoline derivative, a quinoxaline derivative, a phenanthroline derivative, a diazafluorene derivative, and an organic aluminum complex as well as the azafluorene derivative as the material for the organic light-emitting device of the present invention.

An anode material desirably has a work function as large as possible. Examples of the anode material include a metal such as gold, platinum, silver, copper, nickel, palladium, cobalt, selenium, vanadium, tungsten, and alloys thereof, and metal oxides such as tin oxide, zinc oxide, indium oxide, indium tin oxide (ITO) and indium zinc oxide may be used. Further, a conductive polymer such as polyaniline, polypyrrole, or polythiophene may also be used. Each of these electrode substances may be used alone, or two or more of them may be used in combination. Further, the anode may have a single layer structure or a multilayer structure.

A cathode material preferably has a small work function, and includes: for example, alkali metals such as lithium; alkali earth metals such as calcium: simple metals such as aluminum, titanium, manganese, silver, lead, or chromium; and alloys of plural metals, such as a magnesium-silver alloy, an aluminum-lithium alloy, or an aluminum-magnesium alloy. A metal oxide such as indium tin oxide (ITO) may also be used. Each of these electrode materials may be used alone, or two or more of them may be used in combination. Further, the cathode may have a single layer structure or a multilayer structure.

A substrate to be used in the organic light-emitting device of the present invention includes, but is not limited to, an opaque substrate such as a metallic substrate or a ceramic substrate, and a transparent substrate made of glass, quartz or a plastic. In addition, a luminescent color can be controlled by using in the substrate a color filter film, a fluorescent color conversion filter film, a dielectric reflective film, etc.

It should be noted that the produced organic light-emitting device may be provided with a protective layer or a sealing layer for the purpose of preventing the device from coming into contact with, for example, oxygen or moisture. Examples of the protective layer include: an inorganic material film such as a diamond thin film, or a film formed of a metal oxide or a metal nitride; a polymer film such as a polymer film formed of a fluorine resin, polyethylene, a silicone resin, or a polystyrene resin; and a film formed from a photocurable resin. In addition, the device itself may be covered with, for example, glass, a gas impermeable film or a metal, and packaged with an appropriate sealing resin.

A thin film transistor (TFT) may be produced on a substrate, and then the organic light-emitting device of the present invention may be produced to be connected to TFT.

As for the emission direction of the device, it may have a bottom emission structure in which light is emitted from a substrate side, or a top emission structure in which light is emitted from the side opposite to the substrate.

In the organic light-emitting device of the present invention, the layer containing the material for the organic light-emitting device of the present invention and other layers formed from organic compounds are each formed by the following method. A thin film is formed by a vacuum deposition method, an ionized deposition method, sputtering, a plasma deposition method, or a known coating method in which the compound is dissolved in an appropriate solvent. Examples of the coating method to form a thin film include a spin coating, dipping, casting, LB or inkjet method. In particular, when forming a film by a coating method, the film may be formed by using the compound in combination with an appropriate binder resin.

Examples of the binder resin include, but are not limited to, a polyvinyl carbazole resin, a polycarbonate resin, a polyester resin; an ABS resin, an acrylic resin, a polyimide resin, a phenol resin, an epoxy resin, a silicone resin and a urea resin. These binder resins may each be used alone, or two or more of them may be mixed and used as a homopolymer or a copolymer. Further, an additive such as a known plasticizer, antioxidant or ultraviolet absorber may be used in combination as required.

In particular, when an organic layer containing the azafluorene derivative as the material for the organic light-emitting device of the present invention is formed by, for example, a vacuum deposition method or a solution coating method, the layer hardly undergoes crystallization or the like, and is excellent in stability over time.

The layer containing the material for the organic light-emitting device of the present invention is formed into a thin film having a thickness of less than 10 μm, preferably 0.5 μm or less, and more preferably 0.01 to 0.5 μm.

Hereinafter, the present invention will be described specifically by way of working examples. The present invention is by no means limited to these working examples.

Example 1

Synthesis of Exemplified Compound 215

(1) Synthesis of Intermediate Compound M1

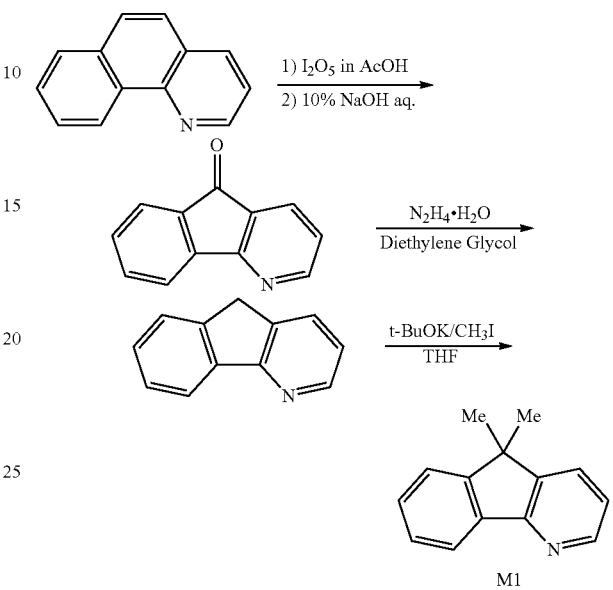

A solution of 68.3 g (381 mmol) of 1-azaphenanthrene and 157 g (470 mmol) of iodopentoxide in acetic acid was stirred under heat at 108° C. for 2 hours. After the reaction liquid had been cooled to room temperature, water was added to the reaction liquid to crystallize the product, and then the crystals were filtered off. Subsequently, the resultant crystal was dissolved in chloroform, washed with an aqueous solution of sodium hydrogen carbonate and an aqueous solution of sodium thiosulfate, dried, and exsiccated by concentration, whereby 53.9 g of 1-azaphenanthrene-5,6-dione were obtained (68% yield).

Subsequently, in a stream of argon, 1.5 L of a 10% aqueous solution of sodium hydroxide was added to 51.0 g (244 mmol) of 1-azaphenanthrene-5,6-dione, and heated and stirred at 85° C. for 90 minutes. After the mixture was cooled to room temperature, the precipitate was filtered out. The filtrate was extracted with chloroform and concentrated, and added to the precipitate, whereby a crude material was obtained. The crude material was purified by chromatography on silica gel with toluene/ethyl acetate=10:1 to give 16.8 g of 4-azafluorene-9-one (37.9% yield).

Subsequently, in a stream of argon, 500 mL of diethylene glycol was added to 16.8 g (92.6 mmol) of 4-azafluorene-9-one and 25 mL (370 mmol) of hydrazine monohydrate, and was heated and stirred at 168° C. for 3 hours. After the reaction liquid was cooled to room temperature, an aqueous solution of sodium chloride was added to the reaction liquid, and then, was extracted with ethyl acetate. The organic phase was washed with water, dried over sodium sulfate and concentrated, to thereby obtain 15.3 g of 4-azafluorene (99% yield).

Subsequently, in a stream of argon, 15.1 g (90.4 mmol) of 4-azafluorene was dissolved in 100 mL of dehydrated THF, and 23.3 g (208 mmol) of tert-butoxypotassium was added to the solution at −11° C. under stirring. After that, the mixture was stirred for 1 hour. Subsequently, 15 mL (208 mmol) of iodomethane were added to the mixture. The temperature of the mixture was raised to room temperature, and the mixture was stirred for 2 hours. After completion of the reaction, water was added to the mixture to terminate the reaction, extracted with toluene, washed with an aqueous solution of sodium thiosulfate and a saturated salt solution, dried over sodium sulfate, and concentrated. The concentrate was purified by treatment with activated clay in a toluene solution, whereby 16.5 g of 9,9-dimethyl-4-azafluorene as Intermediate Compound M1 were obtained (94% yield).

(2) Synthesis of Intermediate Compound M2

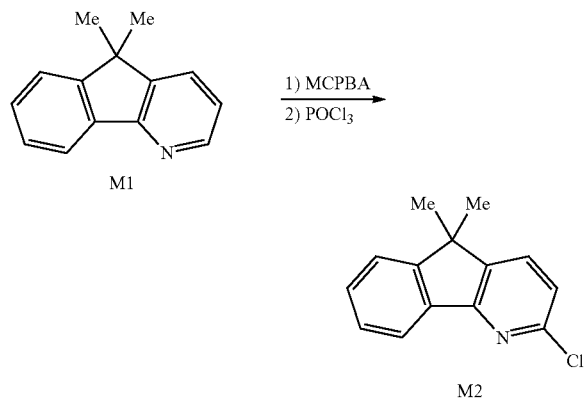

In a stream of argon, 16.45 g (84.3 mmol) of Intermediate Compound M1 was dissolved in 50 mL of chloroform, 30 g (101 mmol) of methachloroperbenzoic acid (MCPBA) was added to the solution at 25° C. with stirring, and stirred at room temperature for 2 hours. After the reaction, sodium thiosulfate was added to the mixture, and dried over sodium sulfate and filtrated. After that, the filtrate was concentrated and the slurry was washed with chloroform, whereby a crude material was obtained. The crude material was purified by chromatography on silica gel with ethyl acetate:methanol=1:1 to give 17.2 g of an N-oxide of Intermediate Compound M1 (97% yield).

Subsequently, 30 mL of phosphorus oxychloride was added to 17.1 g (81.0 mmol) of the above N-oxide, and heated and stirred at 95° C. for 10 hours. After the reaction, the reaction liquid was concentrated, and then chloroform was added to the concentrate. The chloroform solution was added dropwise to a saturated aqueous solution of sodium hydrogen carbonate, and stirred for 1 hour. The mixture was extracted with chloroform, washed with a saturated salt solution, dried over sodium sulfate, and concentrated, whereby a crude material was obtained.

The crude material was purified by chromatography on silica gel with chloroform to give 9.28 g of Intermediate Compound M2 [3-chloro-9,9-dimethyl-4-azafluorene] (50% yield).

(3) Synthesis of Exemplified Compound 215

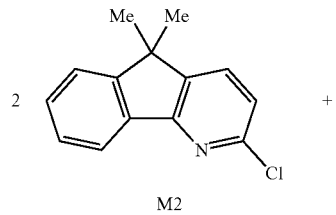

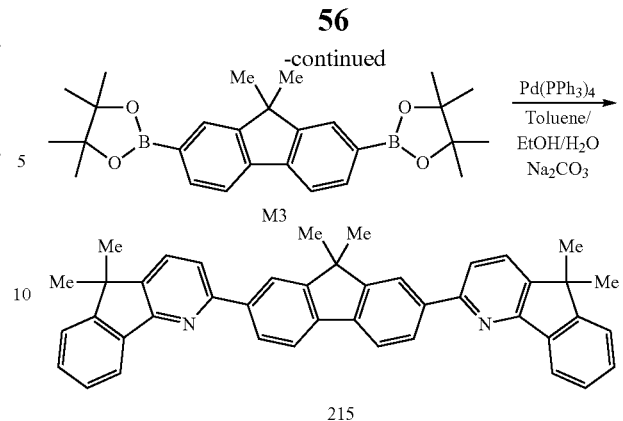

Under nitrogen, the following compounds were added to the mixed solvent of toluene (30 mL) and ethanol (15 mL).
Intermediate Compound M2: 0.60 g (2.61 mmol)
Compound M3 (2,7-bis(4,4,5,5-tetramethyl[1,3,2]dioxaborolan-2-yl)-9,9-dimethyl-9H-fluorene): 0.53 g (1.19 mmol)
Tetrakis(triphenylphosphine)palladium: 0.14 g (0.12 mmol)

Further, 14 mL of a 10 wt % aqueous solution of sodium carbonate were added to the mixture, and heated and refluxed at 69° C. for 10 hours under stirring. After the reaction, the organic phase was extracted with toluene, washed with water, dried over sodium sulfate, and concentrated, whereby a crude material was obtained. The crude material was purified by chromatography on silica gel with chloroform to give 329 mg of Exemplified Compound 215 (48% yield).

Figure 4:
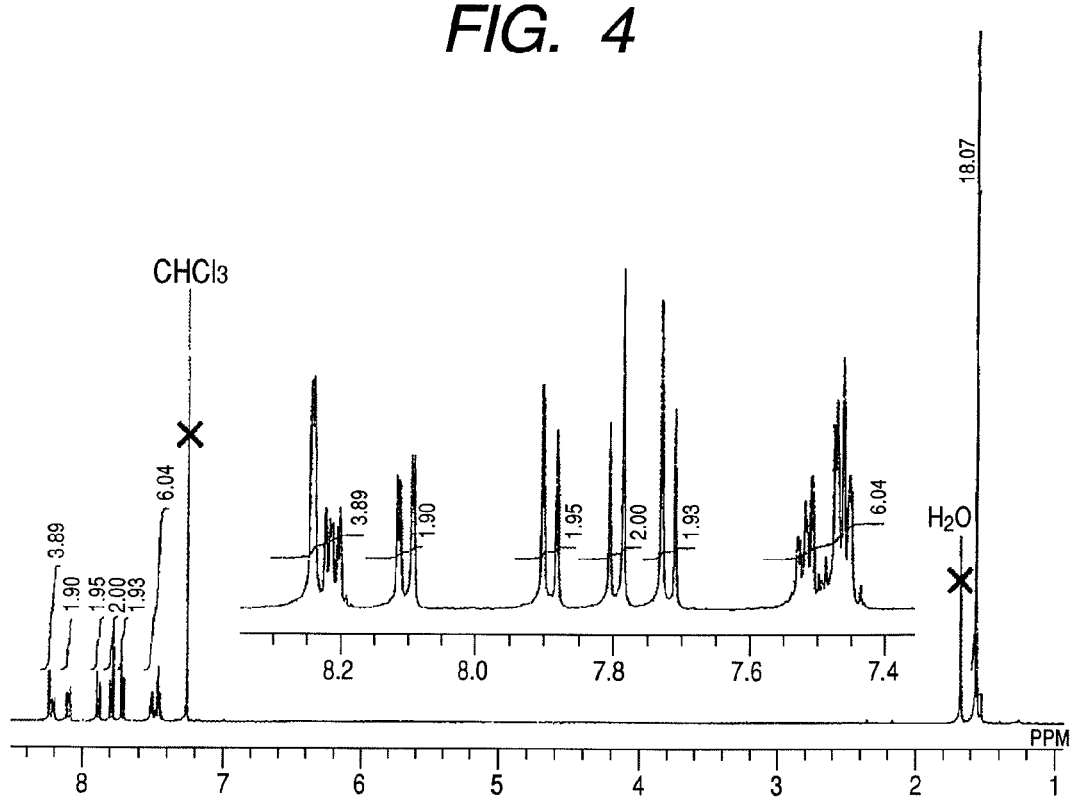
FIG. 4 is a view showing the $^1$H-NMR spectrum (solvent: CDCl$_3$) of Exemplified Compound 215.

The M+ of the compound was identified as 580.3 by matrix-assisted laser desorption/ionization time-of-flight mass spectrometry (MALDI-TOF-MS). Further, the structure of the compound was also identified by $^1$H-NMR measurement. As a result, an NMR spectrum shown in FIG. 4 was obtained.

Further, each of the following exemplified compounds can be synthesized by the same synthesis method as in Example 1-(3).

(Exemplified Compound 101): Exemplified Compound 101 can be obtained in the same manner as in Example 1-(3) except that 2-(4,4,5,5-tetramethyl[1,3,2]dioxaborolan-2-yl)-9,9-dimethyl-9H-fluorene is used instead of Compound M3.

(Exemplified Compound 108): Exemplified Compound 108 can be obtained in the same manner as in Example 1-(3) except that 3,5-diphenylboronic acid is used instead of Compound M3.

(Exemplified Compound 131): Exemplified Compound 131 can be obtained in the same manner as in Example 1-(3) except that: 6-bromo-3-chloro-9,9-dimethyl-4-azafluorene is used instead of Intermediate Compound M2; and 2-(4,4,5,5-tetramethyl[1,3,2]dioxaborolan-2-yl)-9,9-dimethyl-9H-fluorene is used instead of Compound M3.

(Exemplified Compound 233): Exemplified Compound 233 can be obtained in the same manner as in Example 1-(3) except that 2,7-bis[4-(4,4,5,5-tetramethyl[1,3,2]dioxaborolan-2-yl)phenyl]-9,9-dimethyl-9H-fluorene is used instead of Compound M3.

(Exemplified Compound 234): Exemplified Compound 234 can be obtained in the same manner as in Example 1-(3) except that 2,7-bis[3-(4,4,5,5-tetramethyl[1,3,2]dioxaborolan-2-yl)phenyl]-9,9-dimethyl-9H-fluorene is used instead of Compound M3.

(Exemplified Compound 303): Exemplified Compound 303 can be obtained in the same manner as in Example 1-(3) except that 3-quinoline boronic acid is used instead of Compound M3.

(Exemplified Compound 404): Exemplified Compound 404 can be obtained in the same manner as in Example 1-(3) except that 2,7-bis(4,4,5,5-tetramethyl[1,3,2]dioxaborolan-2-yl)-9,9-dimethyl-4,5-diazafluorene is used instead of Compound M3.

(Exemplified Compound 501): Exemplified Compound 501 can be obtained in the same manner as in Example 1-(3) except that 1,3,5-benzene triboronic acid is used instead of Compound M3.

(Exemplified Compound 604): Exemplified Compound 604 can be obtained in the same manner as in Example 1-(3) except that 6-(4,4,5,5-tetramethyl[1,3,2]dioxaborolan-2-yl)-9,9-dimethyl-4-azafluorene is used instead of Compound M3.

(Exemplified Compound 722): Exemplified Compound 722 can be obtained in the same manner as in Example 1-(3) except that 6-bromo-9,9-dimethyl-4-azafluorene is used instead of Intermediate Compound M2.

(Exemplified Compound 907): Exemplified Compound 907 can be obtained in the same manner as in Example 1-(3) except that 2-chloro-9,9-dimethyl-1-azafluorene is used instead of Intermediate Compound M2.

(Exemplified Compound 615): Exemplified Compound 615 can be obtained in the same manner as in Example 1-(3) except that 6-bromo-3-chloro-9,9-dimethyl-4-azafluorene is used instead of Intermediate Compound M2; and 6-(4,4,5,5-tetramethyl[1,3,2]dioxaborolan-2-yl)-9,9-dimethyl-4-azafluorene is used instead of Intermediate Compound M3.

(Exemplified Compound 707): Exemplified Compound 707 can be obtained in the same manner as in Example 1-(3) except that 2,6-dibromo-9,9-dimethyl-4-azafluorene is used instead of Intermediate Compound M2; and 2-(4,4,5,5-tetramethyl[1,3,2]dioxaborolan-2-yl)-9,9-dimethyl-9H-fluorene is used instead of Compound M3 in Example 1-(3).

(Exemplified Compound 812): Exemplified Compound 812 can be obtained in the same manner as in Example 1-(3) except that: 2,7-dibromo-9,9-dimethyl-4,5-diazafluorene is used instead of Intermediate Compound M2; and 6-(4,4,5,5-tetramethyl[1,3,2]dioxaborolan-2-yl)-9,9-dimethyl-4-azafluorene is used instead of Compound M3.

(Exemplified Compound 814): Exemplified Compound 814 can be obtained in the same manner as in Example 1-(3) except that: 2,7-dichloro-1,8-naphthyridin is used instead of Intermediate Compound M2; and 6-(4,4,5,5-tetramethyl[1,3,2]dioxaborolan-2-yl)-9,9-dimethyl-4-azafluorene is used instead of Compound M3.

Example 2

Synthesis of Exemplified Compound 232

In the same manner as in Example 1-(3), under nitrogen, the following compounds were heated and refluxed in a mixed solvent of toluene (25 mL), ethanol (12 mL) and a 10 wt % aqueous solution of sodium carbonate (12 mL) at 68° C. for 6 hours under stirring. Intermediate Compound M2: 0.57 g (2.48 mmol) 3,6-bis(4,4,5,5-tetramethyl[1,3,2]dioxaborolane-2-yl)-9,9-dimethyl-9H-fluorene): 0.50 g (1.12 mmol) Tetrakis(triphenylphosphine)palladium: 0.13 g (0.12 mmol)

After the reaction, the organic phase was extracted with toluene, washed with water, dried over sodium sulfate, and concentrated, whereby a crude material was obtained. The crude material was purified by chromatography on silica gel with toluene/chloroform=1:3 to give 422 mg of Exemplified Compound 215 (65% yield).

The of the compound was identified as 580.3 by matrix-assisted laser desorption/ionization time-of-flight mass spectrometry (MALDI-TOF-MS).

Example 3

An organic light-emitting device having a structure shown in FIG. 3 was produced by the following method.

Indium tin oxide (ITO) was formed into a film having a thickness of 120 nm by a sputtering method on a glass substrate (the substrate 1) so as to serve as the anode 2, and the resultant was used as a transparent conductive supporting substrate. An organic layer and a layer corresponding to a cathode were successively formed on the transparent conductive supporting substrate by vacuum deposition with resistance heating in a vacuum chamber having a pressure of $10^{-4}$ Pa. To be specific, Compound A shown in the following formula was first formed into a film having a thickness of 20 nm so as to serve as the hole transport layer 5. Compound B shown in the following formula was then formed into a film having a thickness of 30 nm so as to serve as the light-emitting layer 3. Next, Exemplified Compound 215 was formed into a film having a thickness of 20 nm so as to serve as the electron transport layer 6. Subsequently, KF was formed into a film having a thickness of 1 nm. Finally, Al was formed into a film having a thickness of 120 nm. The KF film and the Al film each function as the cathode 4.

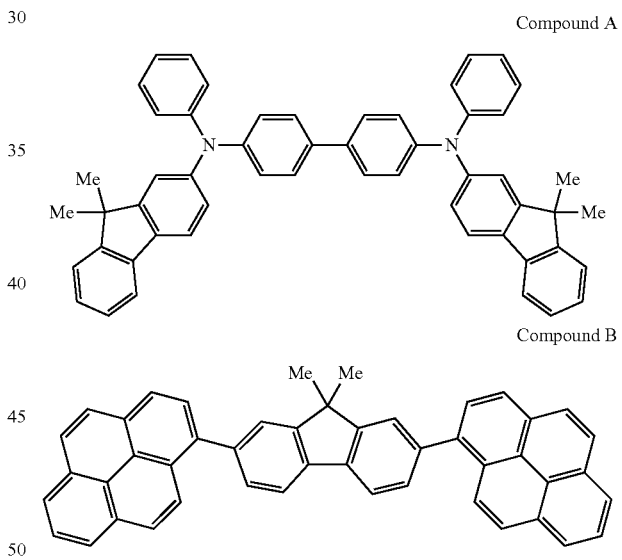

Compound A

Compound B

The resultant organic light-emitting device was covered with a protective glass plate in a dry air atmosphere lest the device should degrade owing to the adsorption of moisture, and was sealed with an acrylic resin-based adhesive.

A DC voltage was applied to the device thus obtained while the ITO electrode (the anode 2) was defined as a positive electrode and the Al electrode (the cathode 4) was defined as a negative electrode. As a result, the device was observed to emit blue light at a low voltage, and showed a small reduction in luminance even after energization for 100 hours.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-349580, filed Dec. 26, 2006, which is hereby incorporated by reference herein in its entirety.

What is claimed is:

1. An organic light-emitting device comprising:
a pair of electrodes composed of an anode and a cathode, either the anode or the cathode being a transparent or semi-transparent electrode, and
an organic compound layer interposed between the pair of electrodes,
wherein the organic compound layer contains an azafluorene derivative represented by following general formula (III):

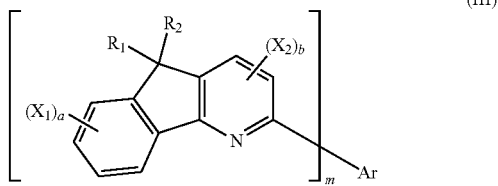

(III)

wherein m represents an integer of 2 to 4, a represents an integer of 0 to 4, and b represents an integer of 0 to 2;
wherein $X_1$ and $X_2$ each independently represent a substituent selected from the group consisting of a substituted or unsubstituted alkyl group, a substituted or unsubstituted alkoxy group, a substituted or unsubstituted aromatic hydrocarbon group, a substituted or unsubstituted heterocyclic group, and a substituted amino group;
wherein Ar represents an m-valent aromatic hydrocarbon group which may be substituted; and
wherein $R_1$ and $R_2$ each independently represent an alkyl group which is unsubstituted or may be substituted by a fluorine atom.

2. The organic light-emitting device according to claim 1, wherein the organic compound layer is an electron transport layer.

3. An organic light-emitting device comprising:
a pair of electrodes composed of an anode and a cathode, either the anode or the cathode being a transparent or semi-transparent electrode, and
an organic compound layer interposed between the pair of electrodes,
wherein the organic compound layer contains an azafluorene derivative represented by following general (IV):

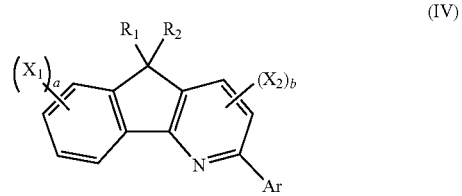

(IV)

wherein a represents an integer of 0 to 4, and b represents an integer of 0 to 2;
wherein $X_1$ and $X_2$ each independently represent a substituent selected from the group consisting of a substituted or unsubstituted alkyl group, a substituted or unsubstituted alkoxy group, a substituted or unsubstituted aromatic hydrocarbon group, a substituted or unsubstituted heterocyclic group, and a substituted amino group;
wherein Ar represents a polycyclic aromatic hydrocarbon group which may be substituted; and
wherein $R_1$ and $R_2$ each independently represent an alkyl group which is unsubstituted or may be substituted by a fluorine atom.

4. The organic light-emitting device according to claim 3, wherein the organic compound layer is an electron transport layer.

5. The organic light-emitting device according to claim 1, further comprising a color filter and a TFT.

6. The organic light-emitting device according to claim 3, further comprising a color filter and a TFT.

* * * * *